(12) United States Patent
Jones et al.

(10) Patent No.: US 11,141,044 B2
(45) Date of Patent: Oct. 12, 2021

(54) METHOD AND APPARATUS FOR ESTIMATING THE VALUE OF A PHYSICAL PARAMETER IN A BIOLOGICAL TISSUE

(71) Applicant: UCL Business LTD, London (GB)

(72) Inventors: Geoffrey Jones, London (GB); Danail Stoyanov, London (GB); Dan Elson, London (GB); Neil Clancy, London (GB)

(*) Notice: Subject to any disclaimer, the term of this patent is extended or adjusted under 35 U.S.C. 154(b) by 260 days.

(21) Appl. No.: 16/310,286

(22) PCT Filed: Jun. 19, 2017

(86) PCT No.: PCT/GB2017/051784
§ 371 (c)(1),
(2) Date: Dec. 14, 2018

(87) PCT Pub. No.: WO2017/216585
PCT Pub. Date: Dec. 21, 2017

(65) Prior Publication Data
US 2019/0320875 A1 Oct. 24, 2019

(30) Foreign Application Priority Data
Jun. 17, 2016 (GB) .................................... 1610594

(51) Int. Cl.
*A61B 1/00* (2006.01)
*A61B 5/1459* (2006.01)
(Continued)

(52) U.S. Cl.
CPC ........ *A61B 1/00009* (2013.01); *A61B 5/1459* (2013.01); *G06T 7/0012* (2013.01);
(Continued)

(58) Field of Classification Search
None
See application file for complete search history.

(56) References Cited

U.S. PATENT DOCUMENTS 7,231,243 B2 * 6/2007 Tearney ............. A61B 1/00082
600/407
9,351,642 B2 * 5/2016 Nadkarni ........... A61B 5/02007
(Continued)

FOREIGN PATENT DOCUMENTS

WO        2009/052607 A1    4/2009
WO    WO-2009052607 A1 * 4/2009 ............. A61B 1/042

OTHER PUBLICATIONS

International Search Report and Written Opinion dated Oct. 6, 2017 for International Application No. PCT/GB2017/051784 entitled "Method and Apparatus for Estimating the Value of a Physical Parameter in a Biological Tissue".
(Continued)

*Primary Examiner* — Anand P Bhatnagar
(74) *Attorney, Agent, or Firm* — Hamilton, Brook, Smith & Reynolds, P.C.

(57) ABSTRACT

A method and apparatus are provided for estimating the value of a physical parameter of biological tissue. The method comprises acquiring a colour image of the biological tissue from a single image capture device; extracting from the colour image at least two images in respective optical wavebands having a different spectral sensitivity from one another, whereby a given location in the biological tissue is present in each of the extracted images; providing a physical model of the optical properties of the biological tissue, wherein the optical properties of the biological tissue are sensitive to the value of said physical parameter; and estimating the value of the physical parameter at said given location based on an intensity value at that location for each extracted image. The estimating utilises the physical model of the optical properties of the biological tissue and the spectral sensitivity for each respective waveband.

19 Claims, 15 Drawing Sheets

(51) Int. Cl.
     *G06T 7/00*    (2017.01)
     *A61B 1/06*    (2006.01)
     *A61B 5/145*   (2006.01)
(52) U.S. Cl.
     CPC ......... *A61B 1/00186* (2013.01); *A61B 1/0638* (2013.01); *A61B 1/0646* (2013.01); *A61B 5/14542* (2013.01); *G06T 2207/10024* (2013.01); *G06T 2207/10068* (2013.01)

(56) References Cited

U.S. PATENT DOCUMENTS

| | | | | |
|---|---|---|---|---|
| 9,998,678 | B2* | 6/2018 | Krattiger | G02B 23/2415 |
| 2002/0035330 | A1* | 3/2002 | Cline | A61B 1/0638 |
| | | | | 600/476 |
| 2005/0065406 | A1* | 3/2005 | Cline | A61B 5/0084 |
| | | | | 600/160 |
| 2008/0228037 | A1* | 9/2008 | Cline | A61B 1/00186 |
| | | | | 600/160 |
| 2010/0111396 | A1* | 5/2010 | Boucheron | G06K 9/6231 |
| | | | | 382/133 |
| 2013/0271591 | A1* | 10/2013 | Van Leest | H04N 7/18 |
| | | | | 348/77 |
| 2014/0155717 | A1 | 6/2014 | Saito | |
| 2014/0300718 | A1* | 10/2014 | Krattiger | G01S 17/894 |
| | | | | 348/68 |
| 2020/0348234 | A1* | 11/2020 | Hendrix | G01N 21/6458 |

OTHER PUBLICATIONS

International Preliminary Report on Patentability dated Dec. 18, 2018 for International Application No. PCT/GB2017/051784 entitled "Method and Apparatus for Estimating the Value of a Physical Parameter in a Biological Tissue".
Nighswander-Rempel et al., "Regional variations in myocardial tissue oxygenation mapped by near-infrared spectroscopic imaging," Journal of Molecular and Cellular Cardiology, 34(9), pp. 1195-1203, 2002.
Claridge et al., "Quantifying mucosal blood vol. fraction from multispectral images of the colon," Medical Imaging 2007: Physiology, Function, and Structure from Medical Images, Proc. of SPIE, vol. 6511, 2007.
Clancy et al., "Multispectral imaging of organ viability during uterine transplantation surgery," Proc. SPIE 8935, Advanced Biomedical and Clinical Diagnostic Systems XII, 2014.
Bouchard et al., "Ultra-fast multispectral optical imaging of cortical oxygenation, blood flow, and intracellular calcium dynamics," Optics express, 17(18), pp. 15670-15678, 2009.
Clancy et al., "Multispectral image alignment using a three channel endoscope in vivo during minimally invasive surgery," Biomed. Opt. Express, 3(10), pp. 2567-2578, 2012.
Wickert et al., "Endoscopic sheffield index for unsupervised in vivo spectral band selection," CARE, pp. 110-120, 2014.
Nishidate et al., "Estimation of melanin and hemoglobin using spectral reflectance images reconstructed from a digital RGB image by the wiener estimation method," Sensors, 13(6), pp. 7902-7915, 2013.
Fawzy et al., "Rapid multispectral endoscopic imaging system for near real-time mapping of the mucosa blood supply in the lung," Biomedical Optics Express, 6(8), p. 2980, 2015.
Bosschaart et al., "A literature review and novel theoretical approach on the optical properties of whole blood," Lasers Med Sci, 29(2), pp. 453-479, 2013.
Bashkatov et al., "Optical properties of human colon tissues in the 350-2500 nm spectral range," Quantum Electronics, 44(8), pp. 779-784, 2014.
Wang et al., "MCML—Monte Carlo modeling of light transport in multi-layered tissues," Computer methods and programs in biomedicine, 47(2), pp. 131-146, 1995.
Fang, "Mesh-based Monte Carlo method using fast ray-tracing in Plücker coordinates," Biomed. Opt. Express, 1(1), p. 165, 2010.
Boulnoism J., " Photophysical processes in recent medical laser developments: a review," Lasers in Medical Science, vol. 1, pp. 47-66, 1986.
Delpy et al., "Estimation of optical pathlength through tissue from direct time of flight measurement," Physics in Medicine and Biology, 33(12), pp. 1433-1442, 1988.
Bro et al., "A fast non-negativity-constrained least squares algorithm," J. Chemometrics, 11(5), pp. 393-401, 1997.
Clancy et al., "Intraoperative measurement of bowel oxygen saturation using a multispectral imaging laparoscope," Biomedical Optics Express 4179, 6(10), 2015.
Guazzi et al., "Non-contact measurement of oxygen saturation with an RGB camera," Biomedical Optics Express 6(9), p. 3320, 2015.
1288 EMVA Standard Compliant, "Standard for Characterization of Image Sensors and Cameras," European Machine Vision Association, www.emva.org/wp-content/uploads/EMVA1288-3.0.pdf, Release 3.0, 2010.
Pascale, D., Color checker data. [Online]. Available: http://www.babelcolor.com/colorchecker-2.htm#CCP2 data. (accessed: May 2016).
Clancy et al., "Multispectral imaging of organ viability during uterine transplantation surgery in rabbits and sheep," Journal of Biomedical Optics, 21(10), 2016.
Daubechies, I., "Ten Lectures on Wavelets," Society for Industrial & Applied Mathematics (SIAM), 1992.
Du et al., "Robust surface tracking combining features, intensity and illumination compensation," International Journal of Computer Assisted Radiology and Surgery, 10(12), pp. 1915-1926, 2015.
Jones et al., "Bayesian estimation of intrinsic tissue oxygenation and perfusion from RGB images," IEEE Transactions on Medical Imaging, 36(7), p. 1491, 2017.
Jones et al., "Inference of Tissue Haemoglobin Concentration from Stereo RGB," MIAR, pp. 50-58, 2016.
Robu et al., "Radiometric calibration for a spectrophotometric analysis pipeline for assessing burns," CRAS (Sep. 2015).

* cited by examiner

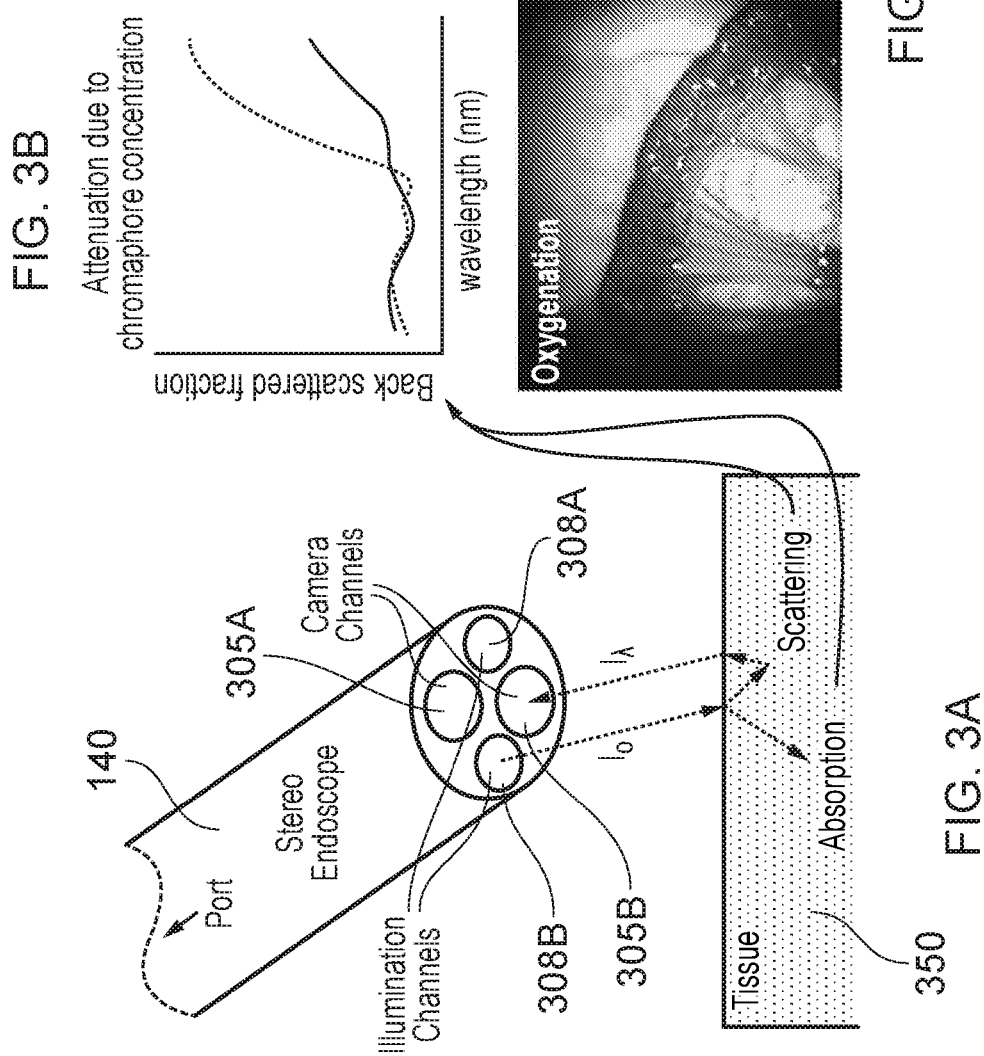

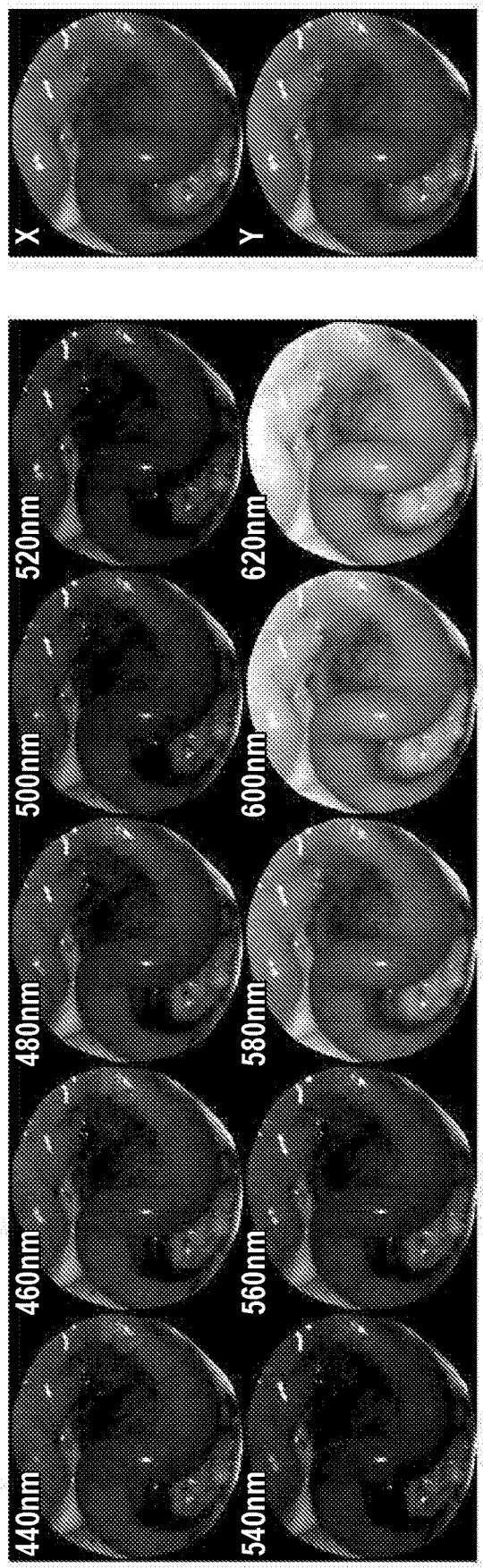
FIG. 14A
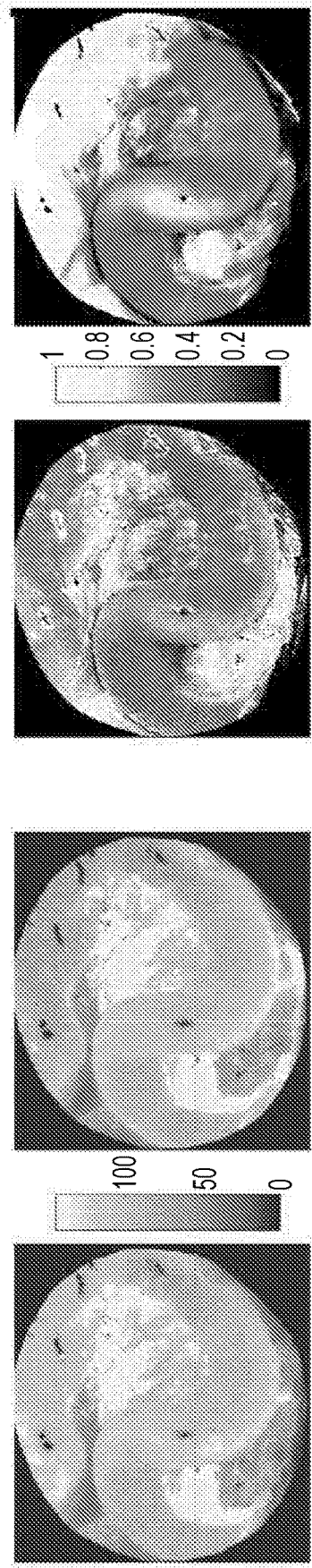
FIG. 14B
FIG. 14C

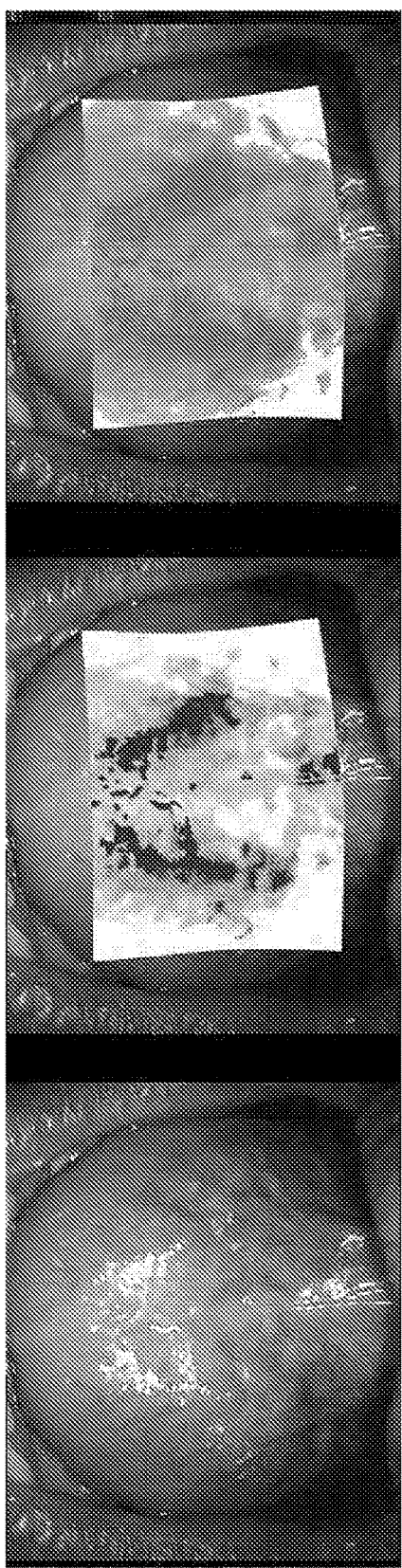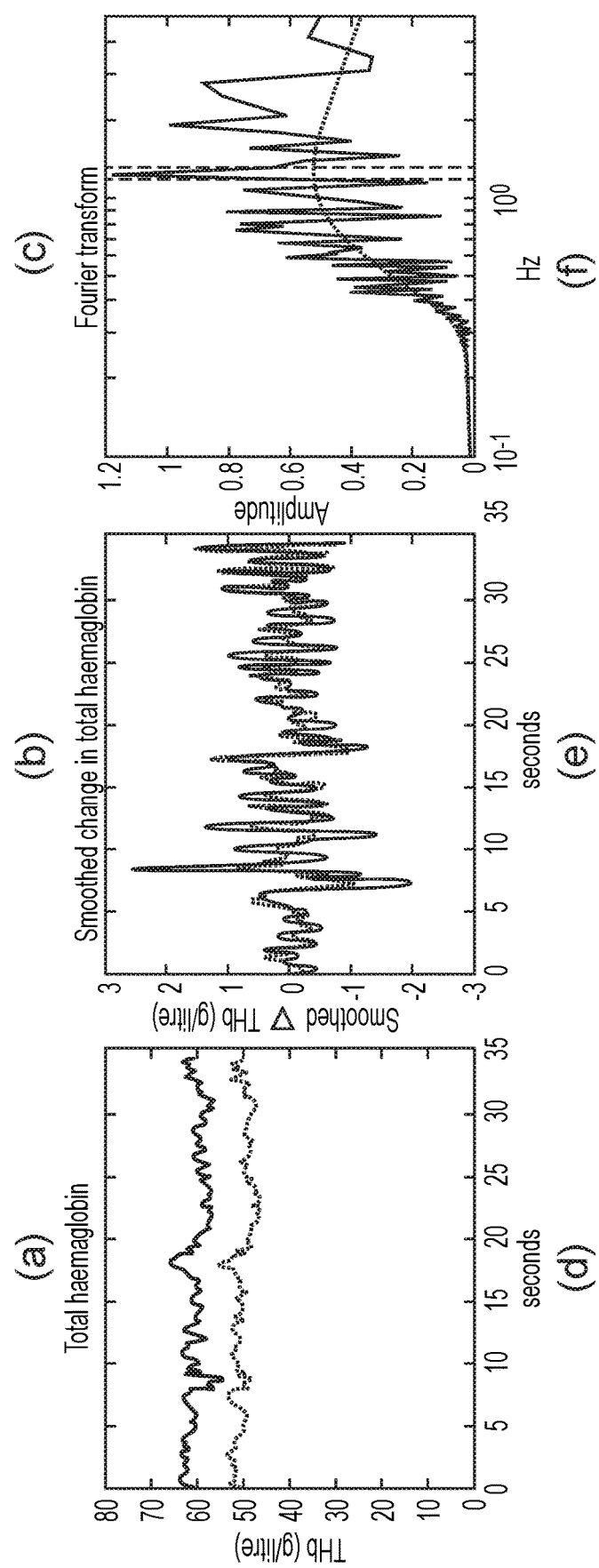
FIG. 15

METHOD AND APPARATUS FOR ESTIMATING THE VALUE OF A PHYSICAL PARAMETER IN A BIOLOGICAL TISSUE

This application is the U.S. National Stage of International Application No. PCT/GB2017/051784, filed Jun. 19, 2017, which designates the U.S., published in English, and claims priority under 35 U.S.C. § 119 or 365(c) to Great Britain Application No. 1610594.2, filed Jun. 17, 2016. The entire teachings of the above applications are incorporated herein by reference.

TECHNICAL FIELD

The present invention relates to a method and apparatus for estimating the value of a physical parameter in a biological tissue.

BACKGROUND

Intra-operative imaging is important for guiding surgical procedures, especially during minimally invasive surgery (MIS). Intra-operative imaging in MIS is often constrained by the number and/or size of incisions or ports, thereby restricting the physical size of the imaging equipment, as well as limiting access by the surgeon to the surgical site. This often constrains the number of possible imaging modalities that can be used concurrently throughout such procedures. Optical colour (three channel RGB) cameras having spectral sensitivity in the visible wavelength range are frequently used during such procedures, occasionally with interruptions to switch to other imaging modalities at specific points during the surgery. One example of a switch in imaging modality would be to identify structural components that are too faint or subtle for the surgeon to detect easily in the RGB image/video.

Several pathological signals, such as melanin and haemoglobin concentration, may correspond to tissue structure and viability, and are detectable by their characteristic attenuation of light in the visible wavelength range. Detecting and displaying this information can then help to provide guidance during a surgical procedure, especially when the variation may not be detectable or quantifiable readily by eye. Visualisation of tissue oxygenation has been used in various procedures throughout the body to provide a surgeon with real-time (intra-operative) information on the oxygenation of tissue in and around the surgical site.

Current white light imaging using endoscopes and laparoscopes is mostly limited to providing information from tissue surfaces, but does not help the surgeon to identify structures within the tissue such as blood vessels or nerves. For example, endoscopic images generally contain only macroscopic structural and radiometric information, but do not directly highlight tissue function or characteristics which may be used to identify malignancy.

Multispectral imaging (MSI) is an attractive modality for intra-operative surgical imaging because it is non-ionising and compatible with common endoscopic instrumentation. MSI has been used to make an in situ assessment of the heart; Nighswander-Rempel et al [1] show how this can be used to measure ischaemia in this sensitive organ without use of ionising radiation. In MIS, imaging the oxygenation of tissue has also been used to help identify malignant tissue, as demonstrated by Claridge et al [2], with the increased vascularisation of malignant tissue resulting in a local increase of the total haemoglobin within tissue. The use of multi-spectral imaging to assess the success of a uterine transplant procedure has been shown by Clancy et al [3], including making inference of the oxygenation saturation and total haemoglobin in the transplanted organ. A similar approach has also been applied to an assessment of bowel perfusion, see Clancy et al [16].

Multispectral imaging has generally been performed using a liquid crystal tuneable filter (LCTF) that separately captures images across multiple narrow (usually non-overlapping) spectral bands. This method of capture is very versatile, but it does require the use of a different camera system, including specialist hardware, during measurement (rather than a standard RGB camera). A further problem with such multispectral imaging is that its temporal resolution is inversely proportional to the spectral resolution. In particular, the serial acquisition at each wavelength enhances spectral resolution but causes signal blur and misalignment when imaging dynamic tissue that is undergoing physiological motion. To compensate for such displacements, Clancy [3] includes a registration step to correct for tissue motion relative to the camera in between the image captures for each spectral band. However, the image registration may still be difficult owing to signal blur and misalignment.

If tissue motion can be completely eliminated, it is possible to ignore factors such as variable tissue morphology and imaging geometry by looking at the change in measurement over time in response to stimuli. This approach has been used by Bouchard et al [4] to image the change in oxygenation in the exposed cortex. The assumption is that after controlling for tissue and camera motion, temporal variation in the scene will be due to changes in concentration of constituent chromophores. As a result the temporal oxygenation signal can be used to make inference about the physical response in the brain to various stimuli, without requiring the injection of any agents into cortex itself. In this work by Bouchard et al [4], variable illumination using strobed light emitting diodes (LEDs) tuned to particular wavelengths allowed for a higher speed capture of the dynamic tissue response; however, the use of such LEDs places a significant demand on the surgical procedure by requiring a specialist lighting environment.

While differing in their practical configuration, the methods of Bouchard [4], Clancy et al [5] and Wickert et al [6] all share a similar theoretical basis. Measurements of the attenuation of illumination across multiple non-overlapping spectral bands are made and, utilising the Beer-Lambert equation, an estimation of chromophore concentration is made. In the case where there is no fluorescence, these techniques are analogous as they all make spectrally distinct measurements of the scene. To estimate the intrinsic oxygenation and total haemoglobin, the optimisation can be posed as a simple least squares fitting, as demonstrated in Clancy [5], using reference reflectance spectra. On the other hand, the use of such methods requires specialist hardware to be installed either alongside or in place of current intra-operative imaging methods in order to perform the spectrally distinct measurements of the scene.

Capturing a full multispectral image of a surgical site with sufficient spectral resolution to allow inference to be performed is therefore typically rather slow, especially if a filter-based approach is being used, since a significant amount of the illuminating light is then filtered out, thereby necessitating relatively long exposure times. Rapid capture through illumination, as used in Bouchard [4], can be achieved by high speed strobe illumination, which generally utilises a carefully chosen set of LEDs that illuminate the surgical site with different narrow spectral bands. However, this again tends to involve specialist hardware.

Rapid filter based approaches such as that of Wickert [6] make use of a reduced number (but maximally discriminative) filter set, to support the rapid capture of a full (polychromatic) image set for making an estimation of the haemoglobin distribution and oxygenation using fewer measurements. However, such an approach generally requires modifications to the existing hardware of most endoscopes or laparoscopes.

Recent rapid capture techniques have focused on the use of RGB (red-blue-green) cameras to capture data at near real-time speeds, by capturing parallel measurements of the surgical site in each channel. The work of Nishidate et al [7] reconstructs intrinsic oxygen saturation ($SO_2$) and total blood volume (THb) from an image obtained from an RGB camera through a two step approach, firstly using a Weiner filtering based reconstruction of the expected spectrum and then obtaining concentrations of chromophores, such as haemoglobin characteristics, through the standard method which is also used for spectrally distinct measurements. This method achieves good results, but is less flexible, since it relies on learning the spectral characteristic for a specific tissue type.

In Fawzy et al [8], a hybrid combination of multiple spectrally distinct bandpass filters and an RGB sensor are used to rapidly sample the spectra or light returning from tissue and capture full multispectral data at high frame rates. This is achieved by using triple band pass filters mounted in a filter wheel to make simultaneous spectrally distinct measurements, recording a set of 18 band filtered measurements in six captures. This framework accounts for spatially varying geometry and achieves a frame rate of 15 fps by a using hardware accelerated (GPU) linear matrix inversion to estimate oxygenation and total haemoglobin distribution. This technique tailors the filters to a specific RGB sensor so again requires a break in surgery to switch imaging modality.

Temporal analysis of tissue directly from RGB video can also be used for the estimation of oxygen saturation, as in Guazzi et al [17]; however this requires sufficient time to detect periodic pathological processes.

The value of multispectral imaging to assist with certain surgical procedures is therefore well-established, but the existing techniques which are available generally have some practical limitations that make them more complex or difficult to utilise in a clinical environment.

SUMMARY

The invention is defined in the appended claims.

A method and apparatus are provided for estimating the value of a physical parameter of biological tissue. The method comprises acquiring a colour image of the biological tissue from a single image capture device; extracting from the colour image at least two images in respective optical wavebands having a different spectral sensitivity from one another, whereby a given location in the biological tissue is present in each of the extracted images; providing a physical model of the optical properties of the biological tissue, wherein the optical properties of the biological tissue are sensitive to the value of said physical parameter; and estimating the value of the physical parameter at said given location based on an intensity value at that location for each extracted image. The estimating utilises the physical model of the optical properties of the biological tissue and the spectral sensitivity for each respective waveband.

Also provided is a non-transitory computer readable medium comprising instructions that, when implemented on a computer, cause the computer to perform the method for estimating the value of a physical parameter of biological tissue as described above.

BRIEF DESCRIPTION OF THE DRAWINGS

Embodiments of the invention will now be described, by way of example only, with reference to the accompanying drawings, in which:

FIG. 3A shows a schematic view of an endoscope and associated illumination for use in estimating the value of a physical parameter of biological tissue in accordance with some embodiments of the present invention.

FIG. 3B shows an example of the spectral distribution of the attenuation of the back-scattered light for the configuration of FIG. 3A.

FIG. 3C shows an RGB endoscopic image of tissue (bottom right). The estimated values of total haemoglobin and oxygenation are determined as described herein, and shown as overlays upon the RGB image (top and left respectively).

FIG. 14A shows a comparison between the selected bands (wavelengths) from a multispectral datacube and corresponding synthesised RGB views (shown on the right of the image and labelled X and Y).

FIG. 14B shows a comparison between the total haemoglobin estimate (g/litre) of tissue obtained from a reference multispectral image (left) and a corresponding estimate from synthesised RGB images (right).

FIG. 14C shows a comparison between the oxygen saturation estimate (%) of tissue obtained from a reference multispectral image (left) and corresponding estimate from synthesised RGB images (right).

FIG. 15(a) shows an original RGB laparoscopic view of the underside of a tongue.

FIG. 15(b) shows the oxygen saturation estimate overlaid on the laparoscopic view of FIG. 15(a).

FIG. 15(c) shows the total haemoglobin estimate (THb) overlaid on the laparoscopic view of FIG. 15(a).

FIG. 15(d) is a graph showing the total haemoglobin estimate (g/litre) as a function of time for the left and right camera feeds used to obtain the RGB image of FIG. 15(a).

FIG. 15(e) is a graph showing the derivative of the left and right camera feeds of FIG. 15(d) as a function of time after smoothing (smoothing is performed due to large amounts of high frequency noise, e.g., roaming high-lights on tissue surface, non-perfect tracking).

FIG. 15(f) is a graph showing a frequency analysis (Fourier transform) of time-series for the estimate of total haemoglobin of FIG. 15(d). Although the signal contains a lot of noise, a fitted polynomial curve (shown in orange) has a peak between 0.76 and 0.84 seconds.

DETAILED DESCRIPTION

Figure 1:
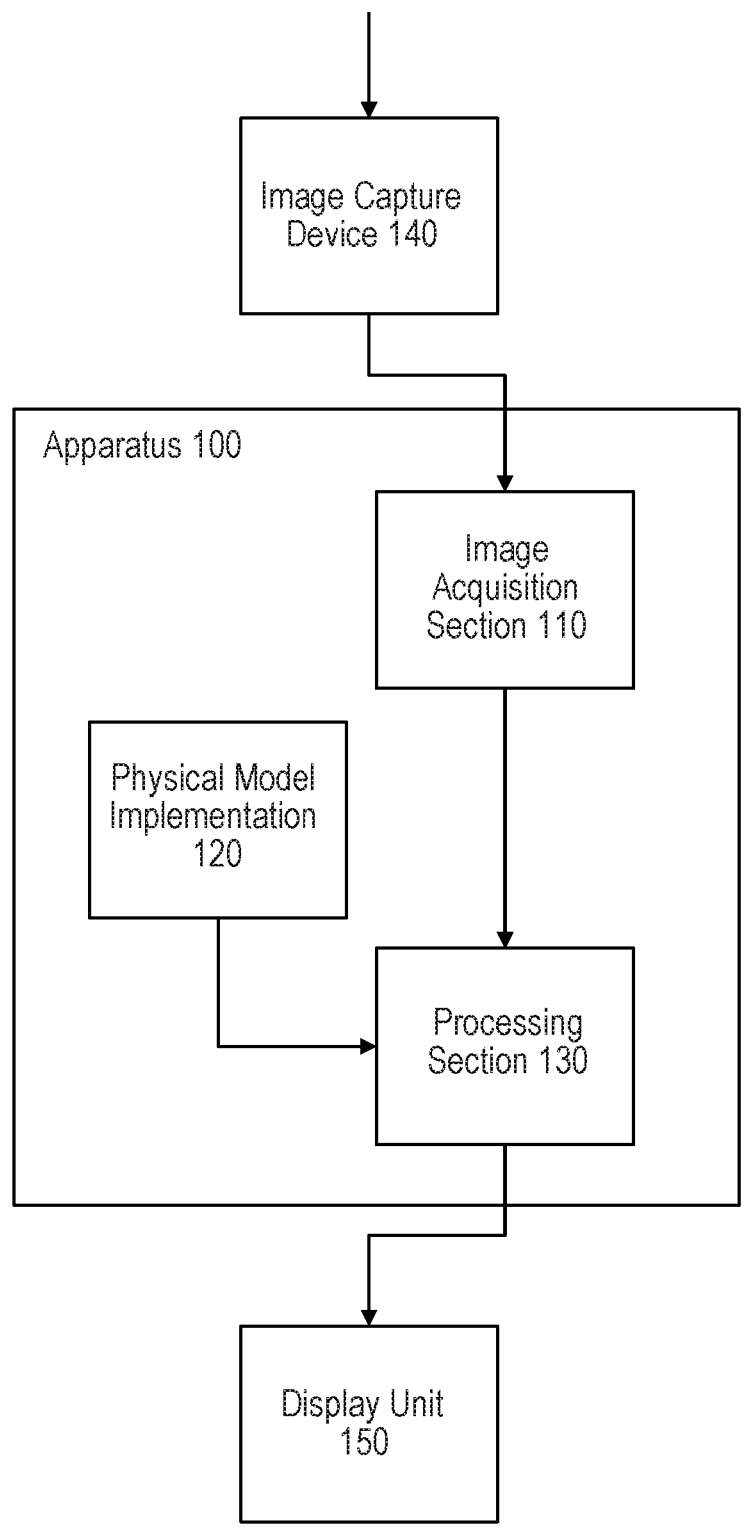
FIG. 1 shows a schematic representation of a system for estimating the value of a physical parameter of biological tissue in accordance with some embodiments of the present invention.

Aspects and features of certain examples and embodiments of the present invention are discussed/described herein. Some aspects and features of certain examples and embodiments may be implemented conventionally and these are not discussed/described in detail in the interests of brevity. It will thus be appreciated that aspects and features of apparatus and methods discussed herein which are not described in detail may be implemented in accordance with any conventional techniques for implementing such aspects and features. We describe herein a technique for recovering values of physical parameters of biological tissue, such as intrinsic measurements of the blood profusion and oxygenation in tissue, from acquired images, such as standard RGB images. In some cases, particularly for RGB images, there may be significant spectral overlap between the waveband of each image (R, G or B), in contrast to many conventional multispectral imaging techniques that have utilised narrow, spectrally distinct images. Detecting and displaying such information regarding in vivo concentrations, etc. could provide a powerful tool to the surgeon, but because the problem is ill-posed when using RGB data, solutions often demand hardware modifications to the endoscopic cameras or lighting to instead capture multispectral data. Various approaches are described herein which seek to help address some of these issues. These approach support estimating a value of a physical parameter of biological tissue which may be used, for example, to provide this information to a surgeon in a real-time or near real-time manner without switching imaging hardware during a surgical procedure.

In some embodiments described herein, the use is made of an RGB sensor/camera or RGB images as the acquired images. Typically, these images are readily available from most endoscope systems which use such RGB images to provide a medical practitioner with a real-time video feed suitable for guiding the endoscope and/or guiding other medical equipment during a surgical operation. As discussed above, traditionally a conventional endoscope must be removed from the patient to allow a multispectral imaging system to be inserted—that is, the imaging equipment must be switched into the subject. However, this adds time, complexity and cost to the overall medical procedure, and/or may also cause more irritation or damage to the subject of the procedure.

In contrast, the present approach makes use of RGB images which are already obtained by (and available from) the endoscope or similar imaging equipment to estimate the value of a physical parameter. Consequently, this approach can be used to supplement an RGB video feed with information regarding the value of the physical parameter across the field of view of the endoscope. Moreover, such an approach typically utilises single shot images, i.e., images obtained in the RGB bands at the same moment in time. It will be appreciated that this approach avoids any switching of the imaging equipment during the medical procedure itself, and also helps to allow the estimated value of the physical parameter to be provided in real-time. This real-time estimation may further be supported by using a look-up table (LUT) that maps all RGB values to a corresponding parameter of interest (for a given configuration).

FIG. 1 shows a highly schematic view of a system for performing multispectral imaging as described herein. In particular, FIG. 1 shows an apparatus 100 which includes an image acquisition section 110, a physical model implementation 120 and a processing section 130. It will be appreciated that the apparatus 100 and components 110, 120, 130 may take any desired form. For example, in one implementation, the apparatus 100 may be general purpose computer (or set of multiple computers) configured by appropriate software to perform the various functionality of components 110, 120, 130. Alternatively, one or more of components 110, 120, 130 may be provided as specific hardware implementations, application-specific integrated circuits (ASICs) or field programmable gate arrays (FPGAs) configured to perform the various functionality of components 110, 120, 130. Further possible implementations of apparatus 100 and components 110, 120, 130, typically formed from suitable combinations of hardware and in software, will be apparent to the skilled person. Apparatus 100 may be further provided with (or connected to) suitable input and/or output means, e.g. a mouse, keyboard, and display screen (not shown in FIG. 1).

Apparatus 100 may be implemented in association with a laparoscope, endoscope or other similar medical equipment used to image biological tissue. The apparatus 100 may be installed or integrated, at least in part, directly into such equipment, or may be utilised in conjunction with such equipment. In this latter case, the apparatus 100 will typically have an appropriate data connection (wired or wireless) to the laparoscope, endoscope or other similar medical equipment.

The image acquisition section 110 is configured to acquire images of biological tissue using or from an image capture device 140. In some implementations, this image capture device 140 is integrated into the apparatus 100, while in other implementations, the image capture device may be a separate unit (albeit connected to transfer the image data into the image acquisition section 110). The image capture device 140 may be configured to take single images and/or continuous (video) images (both of which will be described herein as images). The image capture device 140 may be, for example, include a charge-coupled device (CCD) or CMOS imaging device for obtaining the image signal.

The image capture device 140 is most typically an RGB device, which is able to simultaneously capture an image in three broad, overlapping visible wavebands, denoted red, green and blue. These three RGB images can then be combined to form a full colour image. It will be appreciated that this RGB colour imaging is standard across many electronic optical systems (such as digital cameras, televisions, etc.) and therefore already available as standard on many image capture devices.

Nevertheless, the image capture device 140 is not necessarily restricted to the use of RGB imaging (or formats derived therefrom, such as YUV). For example, the image capture device may capture images (concurrently) in just two optical wavebands, or in four or more optical wavebands. Moreover, these optical wavebands may fall within the visible part of the spectrum, i.e., from 400 nm to 900 nm, or may extend, for example into the UV (up to say 100 nm), and/or into the infrared (up to, for example, 3 μm).

In any event, each of the two, three or more optical wavebands supported by the image capture device has a different spectral sensitivity from the other wavebands. These differing spectral sensitivities for the respective wavebands are typically shifted from one another so as to cover (between them) at least a significant proportion of the visible range. This then allows the images in the different wavebands to be combined to give a composite image that can typically have at least some resemblance to the visual appearance that would be seen by a human. The spectral sensitivity does not necessarily have to be continuous over the whole of a given waveband (e.g. there might not be any sensitivity in the centre of the waveband), although in most implementations the wavebands are indeed likely to be continuous.

In addition, the wavebands are typically relatively broad, e.g. spanning at least 5%, more typically 10% or 20%, of the visible spectrum, to allow shorter exposure times (and hence support real-time imaging). The different wavebands also have a degree of overlap with one another (since this helps to have broader wavebands within a given spectral region).

The images in the different wavebands should be acquired concurrently. In many cases this will involve simultaneous exposure in the different wavebands—for example, conventional RGB cameras frequently have an array of image pixels, which are provided with a suitable spatial pattern of R, G and B filters across the array to obtain the separate colour image in each waveband. Other image capture devices might only acquire a single waveband at a time, but cycle quickly through the different wavebands in order to be able to form a composite video image sufficiently quickly for real-time human viewing—e.g. with a minimum of at least several frames per second, more likely 24 frames per second or higher. A higher frame rate is advantageous in that any temporal variations in the tissue, due to organ movement or the like, within a single image are reduced (thereby improving the quality of the captured images). Moreover, values for the physical parameters of the biological tissue that are derived from the images (as described below) can then be estimated and provided in (near) real-time. Note that having relatively broad wavebands helps to tolerate shorter exposure times, and hence a quicker frame rate for the video.

As noted above, the image capture device 140 may be provided as part of the apparatus 100. In some implementations (or applications), the image acquisition section 110 may acquire the image data in real-time, for example, in an intra-operative environment, thereby providing support for image-guided surgery (or other procedures). In other circumstances, the image acquisition section may acquire the images to analyse retrospectively (i.e. after the relevant clinical procedure has terminated).

The image capture device 140 is configured to provide the image acquisition section with the image data such that the image for each waveband can be separately extracted or identified. It will be appreciated that for RGB images, the R, G and B colour values are saved together for each pixel, so that an image specific to one waveband (R, G or B) can be readily extracted if so desired.

In some cases, the image capture device 140 may be adapted to capture multiple images simultaneously within a given waveband. For example, two RGB images might be obtained that are offset slightly from one another in order to capture a region of biological tissue at slightly different viewing angles or along a different line of sight. These two images can then be used to provide stereoscopic view of the tissue, as described in more detail below.

The physical model implementation 120 is configured to provide and support a physical model of the optical properties of the biological tissue being imaged. These optical properties of the biological tissue are sensitive to the value of a physical parameter of interest, such as the level of oxygenation of blood. More particularly, the way in which light interacts with the tissue (as specified in the physical model) is determined by a given value of the physical parameter. For example, the physical model may include attenuation coefficients indicating how light of a given wavelength that is incident upon the biological tissue is attenuated within the biological tissue dependent upon a given value of the physical parameter. However, the physical model does not require any learned spectral characteristics in respect of a specific tissue type. The physical model implementation, including the attenuation coefficients, is determined in advance using, for example, physical simulation of a given tissue type. Accordingly, the physical model implementation 120 includes or has access to suitable memory or storage for holding the physical model, either locally, e.g. on a hard disk drive or ROM, and/or remotely, e.g. for access over a network such as the Internet.

The physical model generally relates to a tissue type of tissue composition, e.g. the heart or liver, etc., although the model is not specific to an individual patient. In some cases the physical model implementation 120 may provide support for multiple different tissue types, and the appropriate tissue type can be selected in advance for any given clinical procedure. In other implementations, the apparatus 100 may be more specialised for use with a particular organ or tissue type, e.g. the heart, and the physical model implementation 120 may be preconfigured accordingly.

In many cases, the tissue that is being imaged by the image capture device 140 will also be illuminated. Such illumination may be utilised when the image capture device 140 is located inside the body during surgical procedure in order to provide enough light to obtain a useful image. Furthermore, even if a useful image could be obtained without illumination, it may still be desirable to utilise illumination in order to allow shorter exposure times, and hence a better time resolution for the image acquisition. The illumination (not shown in FIG. 1) may be provided by any suitable source device (or combination of such devices), for example, the image capture device 140 itself may provide some form of illumination, and/or this may be provided by some other facility, a light tube, or a light source incorporated into a surgical instrument. The approach described herein does not require any specific type of illumination source, but the illumination should generally be suitable for human viewing of the tissue, for example, providing standard white illumination. However, in practice different sources of white light may provide different spectral distributions of lights (e.g. reflecting different colour temperatures).

The spectral distribution of the light recorded by the image capture device 140 is generally determined by:
(a) the spectral distribution of the illumination (which may be from one or more specific source(s), or from ambient light, or a combination of multiple such sources.
(b) the physical and optical properties of the tissue being imaged (in terms of colour, transparency, etc.), which in turn are sensitive to at least one biological parameter of interest, e.g. the oxygenation of the blood.
(c) the spectral sensitivity of the image capture device 140 in each of the relevant wavebands.

The spectral sensitivity of the image capture device 140 may be provided on a pixel-by-pixel basis (so that each pixel is, in effect, individually calibrated), or as an average across all pixels for an individual device, or as an average across a particular model. The calibration may be provided by the manufacturer (especially at the level of a particular model), and/or may be calibrated by suitable measurements (especially at the level of an individual device). In general, the spectral sensitivity of the image capture device 140 is likely to be reasonably consistent with time, so that the calibration may be a one-off initial measurement, or at least, does not have to be repeated for each clinical procedure.

The spectral sensitivity calibration of the image capture device 140 is obtained for each of the wavebands. In some cases the calibration per waveband may be provided explicitly, in other cases is may be determined from knowledge of the general spectral sensitivity of all pixels, plus knowledge of the spectral (colour) filtering applied to the pixels of each waveband (e.g. to create the R, G and B pixels).

Regarding the spectral distribution of the illumination, the illumination is often provided primarily by a single light source, without a significant contribution from ambient light (because the clinical procedure is internal to the body). In this case, the spectral distribution of the illumination may be provided by the manufacturer of the illumination source (especially at the level of a particular model), and/or may be obtained by suitable measurements of the illumination source (especially at the level of an individual device). Again, such calibration is likely to be reasonably consistent with time.

Another approach is to perform an in situ calibration, e.g. using the image capture device 140 itself. For example, light from the illumination source may be reflected into the image capture device 140 from an instrument surface of known colour (e.g. a white or silver), and this could be used to estimate the spectral distribution of the illumination light (allowing for the spectral sensitivity of the image capture device itself 140). A further possibility is that a sensor is used to measure the spectral distribution of the illumination in situ. Note that this sensor could be relatively compact (since it does not need imaging facilities), and could, for example, be incorporated into the image capture device 140 or some other apparatus, or provided as a standalone device. The use of such in situ measurement may be especially appropriate if there is no dedicated illumination source, for example, if the biological tissue being imaged is illuminated (at least in part) by the general lighting system of the surgical theatre.

In some cases, the calibration information concerning the spectral distribution of the illumination source may be incorporated into the physical model implementation 120, which then in effect represents the overall production of the light that is imaged by the image capture device 140. Likewise, the spectral sensitivities of the image capture device may also be incorporated into the physical model implementation 120. Alternatively, the calibration of the illumination source and/or the calibration of the image capture device 140 may be separately stored in or provided to the apparatus 100 for use by the processing section 130 to perform the analysis described herein.

In general terms, the present approach involves having a known optical input, as per the calibration of the illumination source, and a known optical output, as per the optical signals acquired by the (calibrated) image capture device 140. The optical output is related to the optical input by a transfer function which is dependent on the physical model implementation 120, and more particularly on the at least one biological parameter utilised by this model. This then forms an inverse problem of estimating the at least one biological parameter from the known optical input and the observed optical output.

In some implementations, an iterative approach is used for performing this estimation. In particular, an initial trial value of the physical parameter is assumed, e.g. based on a standard or average biological value. For example, in the case of estimating a concentration of oxygenated haemoglobin as the physical parameter, the initial value may be set as 75 g/l. However, it will be appreciated that this is just an example initial value and other numerical values may be used instead as appropriate.

Taking the initial trial value of the physical parameter as an input to the physical model implementation 120, the processing section 130 uses the physical model implementation to create a predicted image in each waveband (e.g. RGB). The predicted image for each waveband can then be compared with the actual observed image in each waveband, and the result used to update the trial value of the physical parameter. For example, if the predicted images are generally less red than actual images, and it is known that increasing the physical parameter will make the predicted images redder, the trial value can be updated to a larger value. The process then repeats iteratively, updating the trial value at each iteration. When the predicted images have a good match to the observed images (e.g. to within a predetermined threshold), then the algorithm has converged, and the processing stops. At such termination, the most recently updated trial value of the parameter becomes the estimated value of this parameter.

Note that the processing section 130 may perform the above processing separately for each image pixel location to obtain a spatial distribution of the parameter across the image. On the other hand, the processing section 130 may perform the processing on regions of the image, in effect by averaging over multiple pixels. This may give better sensitivity to the actual level of the parameter (by reducing noise), albeit at the cost of lower spatial resolution. Similarly, if a video signal is being received, the processing section may average at a given location over multiple frames of the video, which again may provide better sensitivity to the actual value of the parameter, but at the cost of lower time resolution. (N. B. some form of image registration may be performed to bring into spatial alignment frames or images acquired at different times in order to support such temporal averaging).

In principle, any suitable fitting or estimation technique may be employed to enable the estimated parameter to be obtained from the acquired images. Two exemplary techniques are discussed below in Examples 1 and 2, which disclose a Bayesian approach and a Tikhonov approach for estimating a biological parameter from multispectral data. In some further examples, these estimation techniques can be applied to image data that has first experienced a mathematical transformation, such as a Harr wavelet transformation. In one particular example, the two estimation techniques mentioned above are applied in parallel to different components of the transformed image data.

As shown in FIG. 1, the apparatus 100 is further provided with (or includes) a display 150 which is communicatively coupled to the processing section 130. The display 150 may be remote from the apparatus 100 or may be integrated into the display 150. The communication between the display 150 and the (rest of) apparatus 100 may be over a wired or wireless link.

The display unit 150 can be used to provide a visual display of the biological tissue which is being imaged by the image capture unit 140 (as a video feed or as a succession of individual images, as appropriate). This visual display may comprise two components. The first component corresponds to the conventional image output from the image capture unit 140, for example, a normal RGB camera image. Note that this type of image output is already provided for many clinical procedures, whether for performing some form of investigation (e.g. to look for any sign of disease), or to support some form of intervention (such as for image-assisted surgery).

The second component of the display comprises a map or spatial distribution representing the value of the parameter as determined by the processing section 130 at each location of the image from the image capture device 140. This value can be represented using any suitable display mechanism, e.g. using contours, or colours (such as for a heat map), and so on.

The first and second components may be displayed together for easy comparison, for example, side by side, or one superimposed on the other. In the former case, there may be further tools to help a user identify corresponding locations in each component. For example, a cursor position in one component may be automatically mirrored at the same location for the other component. FIG. 3C (discussed in more detail below) provides an example of the latter approach, in which a colour-scaled image indicative of the value of the physical parameter at each spatial position of the acquired images is used to show total haemoglobin and oxygenation colour-scales overlain upon an RGB image of the same location. Overall, the display allows a clinician to quickly assess the value of the physical parameter associated with a particular region of the image, as well as being able to see a conventional image of that same region.

It will be appreciated that there are a very wide range of further possible options for the display to be provided on display 150, according to the needs and preferences of any given user. For example, the display format may allow the actual numerical value(s) of the physical parameter to be displayed or readily accessed for a given image location—e.g. one option might be to include a text or numerical-based representation of the physical parameter at a selected location of (or adjacent to) the RGB image. Furthermore, a user may be able to display just the first component, or just the second component, or the combination of both (as desired).

Figure 2:
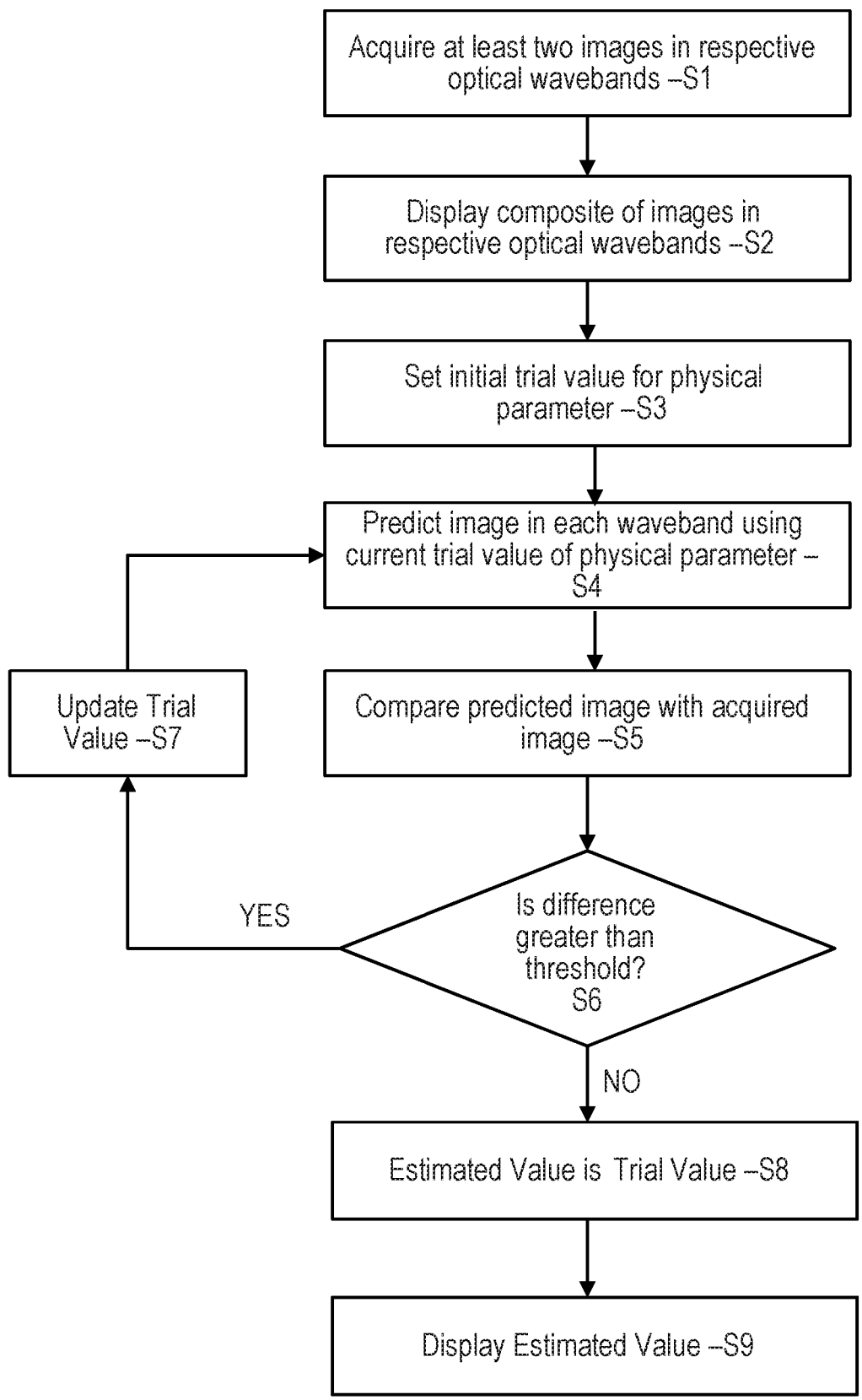
FIG. 2 shows a method for estimating the value of a physical parameter of biological tissue in accordance with some embodiments of the present invention.

FIG. 2 depicts an example method for implementing the approach described herein, such as using the apparatus of FIG. 1. The method begins at step S1 by acquiring two or more images of a biological tissue, each image being acquired in a respective optical waveband a particular spectral sensitivity, such that each image is acquired in a different optical waveband (and hence with a different spectral sensitivity). For example, three images may be acquired, such as red, blue and green. Note that the two or more images are spatially and temporarily coincident with one another—for example, all of the images might be acquired with a single exposure from a single imaging device. This image acquisition may include capturing new images, such as from image capture device 140, and/or accessing stored images, .e.g. from a database or the like containing historical images. The former option may be appropriate for presenting and analysing images in real-time during a clinical procedure, the latter option may be appropriate for analysing the images after the clinical procedure has terminated.

The acquired images may be displayed to a user in composite form (i.e. as a single colour image) at S2. This is particularly appropriate if the acquired images are RGB images or similar, since these images can then be used to provide real-time visualisation of the biological tissue, e.g. as a conventional video feed.

The processing section 130 now utilises the physical model implementation 120 and the acquired images to estimate one or more physical parameters of interest relating to the biological tissue being imaged (having regard to the illumination and spectral sensitivity of the image capture device 140 as discussed above). The physical model implementation 120 takes as input values for the one or more physical parameters, and uses this information to specify a transfer function between the input and output images. In theory we want to go in the reverse direction—determine the one or more physical parameters that would generate the output image given the known illumination (and the physical model of the tissue). However, the model is generally too complex for this estimation to be performed directly, but rather an iterative estimation process can be used instead.

At S3, this iterative process begins by assuming an initial trial value for the physical parameter (or parameters), for example, by taking average value found across multiple subjects, or a previous reading from the same subject.

In S4, the processing section 130 utilises the trial value for the physical parameter(s) in conjunction with the physical model implementation 120 (and knowledge of the illumination and spectral sensitivity of the image capture device) to predict an output image. This predicted output image includes spectral information, thereby allowing the processing section to determine how the predicted image would appear in each of the wavebands.

A comparison is now performed at S5 for each waveband between the predicted image and the acquired image. At S6, a test is performed to see if there is a discrepancy in at least one waveband—e.g. the difference between the predicted image and the acquired image is greater than a set threshold. In this case we take the positive path to S7 and update the trial value for the physical parameter(s). This updating may utilise knowledge of the discrepancy between the predicted image and the acquired image. For example, if increasing the parameter is known to make the tissue appear bluer, then the trial value would be increased if the discrepancy was such that a predicted image was not blue enough compared to the acquired image. We then return to operation S4 and calculate new predicted images, this time with the updated trial value of the physical parameter(s).

It will be appreciated that operations S4, S5, S6 and S7 form an iterative procedure that, all being well, will converge to a value of the physical parameter that allows, in each waveband, the predicted image to match the acquired image (to within the set threshold). At this point we take the negative path from S6 to S8, where the current trial value of the parameter is set as the estimated value of the physical parameter. At S9, this estimated value is then available for display with the acquired images (see S2 above), such as described above in relation to FIG. 1. Alternatively, if there is no convergence, the processing section 130 may abort the procedure after some pre-set number of iterations (not shown in FIG. 2).

Although the processing of FIG. 2 has been described with reference to the entire image, the estimation of the physical parameter can be limited to a particular region of an image (as small as one pixel). Moreover, the approach of FIG. 2 provides one technique for estimating the value of the physical parameter from the observed images. Further techniques are described below that provide a more rigorous statistical basis for such estimation.

One implementation of the technique described here is to provide a single shot capture method utilising a known calibration of the camera to estimate oxygen saturation and the distribution thereof in tissue. The technique is general for internal human tissue in the sense that it does not depend on learned parameters. Instead, in one implementation, the observation in Boulnois et al [13] is used that dominant absorbers for light in the visible wavelength range are oxygenated blood ($HbO_2$—sometimes denoted just as HbO) and deoxygenated blood (Hb), and this provides a prior on the expected spectrum of light leaving the scene.

In a first example below, a technique is presented that can be integrated into a surgical work-flow without the need to switch cameras mid-procedure. This technique is able to run at the frame rate of a standard video camera and to provide information on oxygenated and deoxygenated haemoglobin concentrations within tissue that is commensurate with results that would be acquired through a slower or more disruptive multispectral imaging protocol. Accordingly, the approach described herein offers enhanced integration with current work flows and rapid acquisition of estimated values of physical parameters relating to biological tissue. In a second example below, an estimation tool is presented for measuring the concentration of oxygenated and deoxygenated haemoglobin directly from endoscopic RGB video. The method provides improved accuracy when applied to stereoscopic data but has the versatility to still achieve good results with monocular images. The method performs well on synthetic data and is comparable to the result from raw MSI data acquired using modified imaging hardware such as a LCTF camera. The method makes use of a calibration of optical sensors for a given light source to capture the response curve for each channel. The technique is therefore readily applicable to a wide range of MIS procedures and integrates easily into the operating theatre.

Example 1

The approach adopted in this example involves a single shot capture, and requires no modification to existing surgical imaging configurations. The method of Example 1 uses a radiometric colour calibration of the surgical camera and optical waveband/channel, in conjunction with a Bayesian framework to recover a measurement of the oxygen saturation ($SO_2$). The method is a per-pixel technique that can also incorporate local patch-based information into the estimation of intrinsic $SO_2$ and total blood volume (THb) as physical parameters of clinical interest (a patch represents a small region of the image incorporating, and usually centered on, the pixel of interest). This is done, in this example, by modelling predicted images in each waveband as weighted sums over a mixture of Poisson distributions and optimising the variables $SO_2$ and THb to maximise the likelihood of obtaining the acquired images from the image capture device 140 (or other form of sensor).

In terms of calibrating the spectral sensitivity of the camera, various methods may be utilised. For example, one method to perform a high quality calibration is to use a monochromatic (tuneable) light source [18]. A simpler and quicker method, typically more suited to use in a clinical (rather than laboratory) environment is to use the camera to image a set of coloured patches [19] that have known reflectance, although this latter approach is generally less accurate at higher sensor (camera) noise levels. From simulations, it has been found that a miscalibration of the spectral response curve for the camera tends to bias the optimisation towards deoxy haemoglobin (Hb), whereas the measurement of total haemoglobin was found to be more robust against any such calibration problems.

The technique of this example has been validated on synthetic image data which has been generated from the measured optical characteristics of blood (see Bosschaart et al [9]) and sub mucosa (see Bashkatov et al [10]). Secondly, the method of this example has also been validated on in vivo data by using the multispectral optimisation of Clancy [5] as the ground truth and, in so doing, it is shown how the method of this example correlates strongly with conventional multispectral approaches.

Monte Carlo for Multi-Layered media (MCML) simulation, as shown by Wang et al [11], is an established method for simulating light transport through layered turbid media. The Mesh based Monte Carlo (MMC) approach of Fang et al [12] develops a more expressive simulation framework from this basic approach in order to allow more complex three-dimensional structures to be modelled. It is this latter approach (MMC) that is used herein to simulate a tissue model that is geometrically complex.

Tissue Model

FIG. 3A is a schematic diagram of an image capture device 140 such as for use with apparatus 100 of FIG. 1 for imaging biological tissue. In particular, FIG. 3A shows the passage of light through a turbid media, such as human tissue, which can be considered as a random process comprising scattering and absorption events. Inhomogeneity in the concentration of chromophores results in a spatially varying distribution of detected light. The effective attenuation of a sample will be a combination of the attenuation due to absorption as well as scattering, i.e., how much light of a given wavelength is backscattered out of the tissue again.

FIG. 3B shows the spectral distribution of the light leaving tissue such as shown in FIG. 3A. It can be seen that this spectral distribution can be used to characterise the tissue that the light passes through. In particular, FIG. 3B illustrates the effective attenuation of a uniform white illuminant after backscattering through oxygenated ($\xi_{HbO2}$), and de-oxygenated ($\xi_{Hb}$) blood. These effective backscatter spectra were generated through Monte Carlo simulation.

FIG. 3C shows maps of the tissue saturation and the concentration of oxygenated blood, such as may be generated by the approach described (see below for more detail). An original endoscopic view is shown bottom-right, while the saturation, which is the ratio of oxygenated blood to total haemoglobin, is superimposed (top) on this original endoscopic view. Similarly, the concentration of oxygenated blood is superimposed (bottom-left) on the original endoscopic view. (Note that the total haemoglobin is a measure formed by the sum of concentrations of the two chromophores, oxygenated and de-oxygenated blood).

Returning to FIG. 3A, the image capture device shown therein is a stereo RGB endoscope, which has two camera channels side by side, 305A, 305B. Each camera channel acquires an RGB image, in the sense that a single image (snapshot) can be considered as comprising the superposition of an R image, a G image and a B image (which can be individually extracted from the resulting image). The image capture device 140 includes two illumination channels 308A, 308B, on either side of the two camera channels 305A, 305B. The illumination channels 308A, 308B provide an initial illumination, denoted $I_0$, onto a biological tissue 350 of interest. The camera channels 305A, 305B then receive a return signal (from reflection and scattering, etc), denoted as $I_\lambda$. In particular, the light arriving at the camera channels 305A, 305B is assumed to have been back-scattered and attenuated from passing through the biological tissue 350 containing spatially varying concentration of chromophores (where this concentration of the chromophore can be considered as a physical parameter of interest). In tissue found inside the body, the dominant chromophores are generally the two oxygenation states that haemoglobin can take, the concentration of which can be written as $\xi_{HbO2}$ and $\xi_{Hb}$ for oxygenated and de-oxygenated states respectively.

At a given scene (image) location, x (as imaged by the image capture device 140), the concentration $\xi(x)$ of a given chromophore within the tissue being imaged can be estimated using the modified Beer-Lambert relationship, see Delpy et al [14]. This provides a relationship for how the concentration of all chromophores present in a sample (the tissue at position x) attenuate the incident light $I_{0,\lambda}(x)$ of a given wavelength A arriving at that location.

To produce the resulting intensity of light leaving the scene at that position, $I_\lambda(x)$:

$$I_\lambda(x) = I_{0,\lambda}(x) e^{(-G(x) - \Sigma \xi(x) u_{\xi,\lambda} a_{\xi,\lambda})} \quad (1)$$

This modified form of the Beer-Lambert relationship introduces two notable additions to the original Beer-Lambert equation. The first new variable is the mean path length of light travelling through tissue, $\mu_{\mu,\lambda}$, which together with the attenuation coefficient $a_{\xi,\lambda}$, depends on the wavelength and tissue composition. The second extension is to include a geometry factor G(x) to describe the effect of the surface of the tissue not necessarily being normal to the incident light direction or sensor 140.

Rearranging the terms of (1) it is possible to frame this as a linear relationship:

$$A_\lambda = -\log\left(\frac{I_\lambda(x)}{I_{0,\lambda}(x)}\right) = G(x) + \sum \xi(x) \mu_{\xi,\lambda} a_{\xi,\lambda} \quad (2)$$

where $A_\lambda$ is the attenuation at a given wavelength. This negative log ratio of the incident to exit intensity is the total attenuation A. Thus if the incident illumination is known, the chromophore concentration parameters $\xi(x)$ on the right can be found by making many spectrally distinct measurements of the tissue and solving the linear equation.

$$A = b\xi(x) \quad (3)$$

Here b is a vector of the constants of mean travel distance and attenuation due to chromophores and geometry, for all wavelength measurements in A.

Sensor Model

The probability that a light sensor, such as image capture device 140, detects photons is dependent on two random variables: firstly the chance that a photon left the scene from location x, for which the concentration is $\Xi(x)$, and arrived at the sensor $I/(x,\xi(x))$, and secondly whether the sensor will detect it, $\rho$. In this case the camera sensitivity $\rho$ is assumed to be constant in time but may vary over wavelength. Hence, since this is a counting problem, the probability distribution of the sensor can be represented as Poisson $(\rho_\lambda \cdot E[I_\lambda(x,\xi(x))])$ for any given wavelength, where $E[\cdot]$ represents the expectation of the random variable.

For a wide band detector, such as an entire waveband or channel (c) of a colour sensor, this is then the weighted sum over the sensitive range of wavelengths, with weights corresponding to the sensitivity $\rho_{c,\lambda}$ at that particular wavelength. The random variable of the channel measurement, $I_c(x,\xi(x))$, can be written, for some position x and concentration parameters $\xi$, as the inner product over all wavelengths:

$$I_c(x,\xi(x)) = (\rho_c, I(x,\xi(x)))_\lambda \quad (4)$$

This is a relatively straightforward sum because the contributions from different wavelengths are independent when conditioned on the scene (concentration) parameters $\xi(x)$. The distribution of this random variable is also Poisson distributed with a mean and variance:

$$\mu_c = \sigma_c^2 = \sum^\lambda \rho_{c,\lambda} E[I_\lambda(x)] \quad (5)$$

The random variables for sensor measurements are conditioned on the unknown scene parameters $\xi(x)$ (i.e. the physical parameter(s) of interest) at a given position.

To find the unknown scene parameters, the Bayes rule can be used to find an expression for $\xi(x)$ conditioned on the sensor (camera) measurements in multiple channels. For a three channel (RGB) sensor, the standard Bayes rule gives the relationship:

$$P(\xi \mid I_r, I_g, I_b) = \frac{P(I_r, I_g, I_b \mid \xi) P(\xi)}{P(I_r, I_g, I_b)} \quad (6)$$

where P(•) is a probability. Further due to the channel response being independently conditioned on the scene parameters the right hand side of equation (6) can be formulated as:

$$\frac{P(I_r \mid \xi)P(I_g \mid \xi)P(I_g \mid \xi)P(\xi)}{P(I_r, I_g, I_b)} \quad (7)$$

This gives the product of measurement probabilities for each individual waveband or channel and a prior of the scene parameters ($\xi(x)$). Since each channel accumulates over a wide wavelength range the mean will be quite large, and hence the channel distribution (as per Equation (5)) can be approximated as a normal $N(\mu,\sigma)$.

To estimate the parameter(s) $\xi$ that maximise equation (7), and since the denominator does not depend on $\xi$ and hence can be ignored for the purposes of maximisation of $\xi$, theta is maximised for:

$$\arg\max_{\xi} \left\{ P(\xi) \prod^c N(\mu_{c,\xi}, \sigma_{c,\xi}) \right\} \quad (8)$$

We choose the (prior) distribution of $\xi$, i.e. $P(\xi)$ such that the oxygen saturation ($\xi_{HbO2}/(\xi_{Hbo2}+\xi_{Hb})$) is uniform in the range (0,1), while the total haemoglobin ($\xi_{HbO2}+\xi_{Hb}$) is uniform in the range (0, 250) g/litre. Alternatively, the only prior on may be that all elements are non-negative, given that it is not possible to have negative concentrations. While this may seem too relaxed a constraint allowing concentrations to be potentially infinite, the cases when this might occur are generally limited to degenerate situations where the count for each channel of the sensor is zero or very close to zero. The other term in the maximisation of equation (8) represents, for each waveband, c, the probability of receiving the observed intensity level, which is dependent upon the waveband itself (known), and the concentration parameter $\xi$ (with the summation then being performed over all observed wavebands). Equation (8) then determines the value of the concentration parameter(s) $\xi$ that maximise the likelihood of seeing the set of observed intensities across the set of wavebands c.

Parameter Optimisation

To estimate the concentration, based on Equation (8), from acquired images or channels of RGB measurements, a two-step process is utilised. Since the modified Beer-Lambert model is applicable when measurements are non-overlapping and narrow banded, firstly an estimate of the spectrum of incidental light $I_\lambda'$ arriving at the RGB sensor (or image capture device 140) is obtained. Secondly, an estimate of the concentration of oxy- and deoxy-haemoglobin $\xi$ (vector) from $I_\lambda'$ is obtained by solving equation (2) by minimising sum of square difference (SSD). This process is iterated alternately estimating the multispectral data $I_\lambda'$ and then the concentrations $\xi$.

(It will be appreciated that this is a more sophisticated approach of estimating $\xi$ than the approach illustrated in FIG. 2, in that the latter assumes $I_\lambda'$ is directly as measured by the camera, subject to calibration of the camera. In contrast, in this example it is also recognised that the camera measurement of $I_\lambda'$ is itself subject to uncertainty in view of the Poisson distribution of photon reception).

The first step of estimating the spectrum of incident light is performed using Bayesian maximum a posteriori (MAP) estimation as per the following equation (derived from equation (8), having regard to the relationship between $I_\lambda'$ and $\xi$.

$$I_\lambda' = \arg\max_{I_\lambda} \left\{ \left( \prod^c N(\mu_{c,I_\lambda}, \sigma_{c,I_\lambda}) \right) P(I_\lambda) \right\} \quad (9)$$

During this step, the constraint that $I_\lambda'$ has to adhere precisely to a spectrum predicted by the Beer-Lambert relationship is relaxed, but $I_\lambda'$ is instead penalised through the prior $P(I_\lambda)$. The prior is generated from the previous estimation of using $\xi$ equation (1) to estimate the absorption. We set the penalisation as the SSD between $I'_\lambda$ and the expected value of $E[I_\lambda]$, as predicted by the estimate of the previous iteration for $\xi$. Further, a Dirichlet boundary condition is imposed on $I'_\lambda$ thus limiting the range of the variable to the interval $[0,I_{0,\lambda}]$.

Implementation Details

The optimisation may be performed in various ways—two examples are described below.

Optimisation Method 1

This is an optimisation of equation (9) performed by steepest gradient descent, computed via finite difference as shown in Algorithm 1, which is in essence an expectation maximisation process.

| Algorithm 1: Bayesian estimation of haemoglobin |
| --- |
| input: rgb ← camera measurement |
|              C ← camera response matrix |
| output: hb → oxy/deoxy haemoglobin |
| 1   hb ← initialise with [75g/l, 75g/l] |
| 2   $n_\lambda$ ← the number of wavelengths spanned by C |
| 3   for i ← 0 to 20 do |
| 4       inc ← $n_\lambda$*pow(2,-i) |
| 5       $I_\lambda'$, $I_\lambda$ ← estimate from hb |
| 6       p ← P($I_\lambda'$ | $I_\lambda$,C,rgb) |
| 7       while iterations++ < max and not localminima do |
| 8            x ← arg max$_x$\{P($I_\lambda'$ | $I_\lambda$,C,rgb) | $I_{\lambda,x}$+inc\} |
| 9            $I_{\lambda,x}$+inc |
| 10        if p ≥ P($I_\lambda'$ | $I_\lambda$,C,rgb) then |
| 11               localminima ← true |
| 12        End |
| 13    End |
| 14    hb← estimate from $I_\lambda'$ |
| 15   End |

The gradient descent is not performed using an impulse basis as we found that this provides relatively poor convergence, possibly due to impulse basis increments being close to orthogonal to the space of possible $I_\lambda$. Thus the impulse basis gradient descent converges to a $I_\lambda$ which is a metamerism of the true $I_\lambda$, and the re-estimation linear fitting step (line 14) then produces poor results as it is unlikely that it can fit well to the metameristic $I_\lambda$. (A metamerism is two colours that are perceived as the same, in this case via their RGB signal, but are in fact different in terms of their overall spectral distribution).

Instead a basis change from an impulse basis to a Fourier basis is performed, which was chosen as the space of possible $I_\lambda$ is sparse in Fourier representation. This basis change is possible because of independence in the impulse basis representation, and this is preserved when switching to another linear independent basis representation during the optimisation. This is a rewriting of the solution to equation (9), using steepest gradient descent:

$$\nabla_R \left( \prod^c N(\mu_{c,I_\lambda}, \sigma_{c,I_\lambda}) \right) P(I_\lambda) \quad (10)$$

to now be:

$$\nabla_{\mathcal{F}} \left( \prod^c N(\mu_{c,I_\lambda}, \sigma_{c,I_\lambda}) \right) P(I_\lambda) \quad (11)$$

where the only change required is the basis in which partial derivatives are calculated.

This is essentially exploiting how a Fourier basis better approximates the non-linear basis of the space of possible $I_\lambda$ than an impulse basis and is more likely to converge to a solution that within the space of plausible $I_\lambda$. Further the convergence is faster because the space of possible $I_\lambda$ is sparse in a Fourier basis.

Hence steepest gradient descent is performed in Fourier space maintaining sparsity characteristics of the expected power spectra. Thus at each step of the gradient descent the estimated spectrum $I_\lambda'$ is still a highly probable spectrum, resulting in a significantly better re-estimation step.

Finally the fast non-negative least squares method of Bro et al [15] is used to solve the parameter estimation from the estimated emission spectrum. Non-negativity is required as it would not be physically plausible to have negative concentrations of chromophores. Further, this method is efficient on small matrices.

Optimisation Method 2

In a second optimisation method, equation 9 is optimised using a more direct approach. Instead of using gradient descent as in optimisation method 1, optimisation method 2 concatenates the camera matrix with a scaled identity matrix and solves as a linear optimisation.

Using the understanding that each of the per channel variables is maximised when the difference is minimised between $\langle \rho_c, I_\lambda \rangle$ and the measurements made in each channel, and that the contribution of the prior is to penalise per wavelength deviation of $I_\lambda$ from the current estimate, we can pose the minimisation:

$$I_\lambda' = \arg\min_{I_\lambda} \left\{ \sum^c (\langle \rho_c, I_\lambda \rangle - I_c)^2 + \sum^\lambda (I_\lambda - E[I_\lambda])^2 \right\} \quad (9a)$$

The expected value of $I_\lambda$, $E[I_\lambda]$ is as predicted by equation (1) from the previous iterations estimate for $\xi$. Further, the approximation of the Poisson distribution by the Normal could potentially allow negative count values for each wavelength, so a non-negativity constraint on $I_\lambda'$ is imposed to prevent physically impossible values.

The optimisation of equation 9a can then be achieved via a single linear expression solving for $I_\lambda'$ on the left hand side below:

$$\begin{bmatrix} \gamma & & 0 \\ & \ddots & \\ & \rho_{r,g,b} & \\ 0 & & \gamma \end{bmatrix} I_\lambda' = \begin{bmatrix} \gamma E[I_\lambda] \\ I_r \\ I_g \\ I_b \end{bmatrix} \quad (9b)$$

where $I_r$, $I_g$, and $I_b$ are the sensor measurements in each channel, and $\gamma$ is a regularisation constant. To prevent the prior dominating, $\gamma$ is set to 0.01 (although other values may be set). Since the left hand side of equation 9b is constant over all iterations, this is a computationally efficient approach as decompositions of the left hand matrix can be reused each time. A fast non-negative least squares method is used to solve equation 9b and also for the subsequent parameter estimation.

This optimisation method can be summarised in a similar algorithm to Algorithm 1. In this case, lines 6 to 13 of Algorithm 1 become: $I_\lambda' \leftarrow$ estimate from C, rgb, $I_\lambda$.

Real-Time

The above optimisation is deterministic when you set as fixed the illumination spectrum and the response curves of the colour channels (wavebands) of the camera. In other words, there is a fixed correspondence between the (estimated/measured) $I_\lambda$ and the chromophore concentration $\xi$. Accordingly, the algorithm can be performed in real time by use of a pre-computed look-up table (LUT) that maps all possible RGB values to a corresponding chromophore concentration $\xi$.

Using such a look-up table consisting of all possible 24-bit RGB colours (approximately 16 million), it was feasible to process endoscopic images at video rate using a naive serial implementation. The look-up table in this case was 270 MB in size, and so would easily integrate into a GPU-based live video processing pipeline on currently available hardware. Using a Surface Pro 3 2.3 GHz 8 GB RAM, it was feasible to process images over 30 fps using a two threaded serial implementation of the LUT based approach.

Experiments and Results

Synthetic Data Experiments

To create synthetic test data, multi-spectral image data was created and then filtered to generate RGB camera responses. The optical characteristics of blood and colonic submucosa (soft tissue) were compiled from Bosschaart [9] and Bashkatov [10] respectively. The synthetic phantom model comprised a homogeneous block of soft tissue with three superficial vessels containing either oxygenated or de-oxygenated blood. The three blood vessels had different uniform diameters of 2 mm, 1 mm, and 0.5 mm respectively, and the top edge of each vessel was at the same depth below the surface of the tissue. The data generation was repeated three times with different depths of submersion for the vessels, namely: 1 mm, 2 mm, and 5 mm.

Figure 4A:
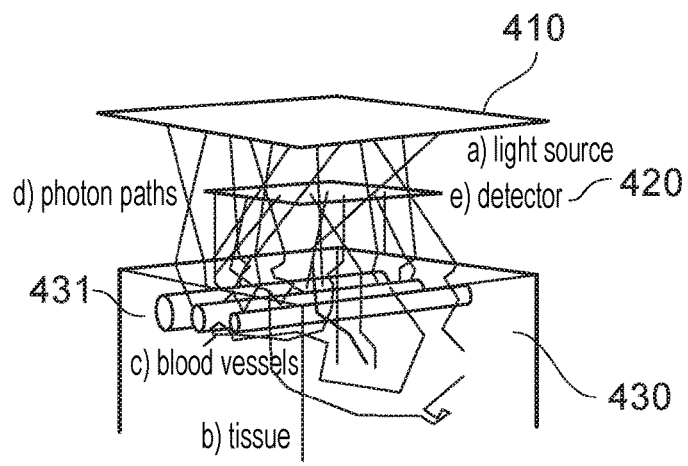
FIG. 4A shows a representation of an experimental (simulated) model of biological tissue, including blood vessels, used for investigating the approach described herein.

The Mesh based Monte Carlo (MMC) simulation of Fang [12] was used on a meshed version of the digital phantom model shown in FIG. 4A. In particular, FIG. 4A shows a representation of an experimental model comprising an isotropic planer (40 mm square) light source 410 (a) and a soft tissue volume 430 (b, 100 mm cube). Inset into the tissue 430 are three parallel blood vessels 431 (c) at constant depth. The interstitial space within the simulation volume is given the properties of air. Photon trajectories (d) are tracked until they leave the simulation volume or arrive at the detector 420 (e), which is 20 mm wide square, parallel to, and 10 mm away from, the tissue surface).

For the MMC, the mesh was made denser near the blood vessel boundaries for smoother approximation of the curved vessel walls. For the MMC simulation, photons were generated at intervals of 10 nm across the range 400 nm to 900 nm. To detect the backscattered light photon momentum was recorded for all photons leaving the bounds of the meshed region. Photons that did not exit through the side of the mesh that was illuminated were discarded, as were photons leaving at an angle to the surface that was too oblique to be detected by a detector placed 10 mm above the illuminated surface. Image data for each wavelength were then generated at this detector location.

Figure 4C:
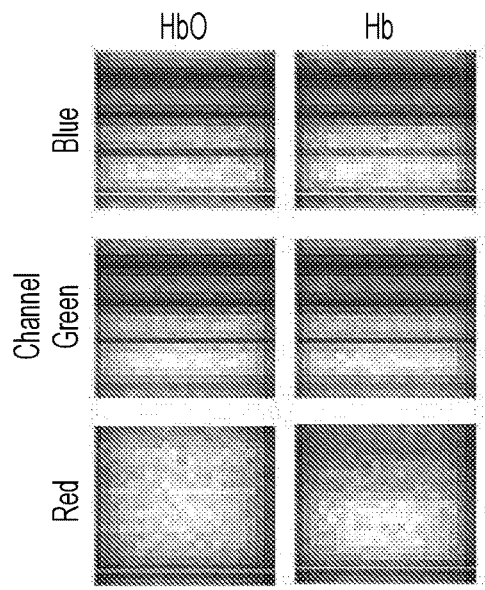
FIG. 4C shows how the configuration of FIG. 4A appears if the blood is (i) oxygenated (left), or (ii) de-oxygenated (right), in each of the R, G and B wavebands (bottom, middle and top respectively according to the spectral response curves of FIG. 4B.
Figure 4B:
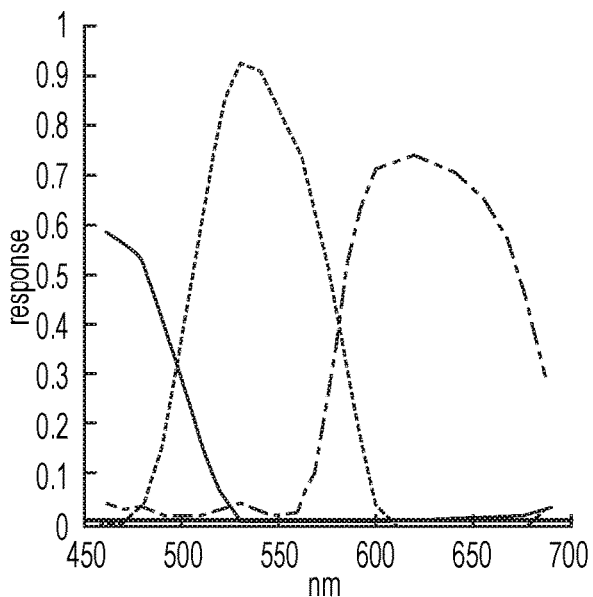
FIG. 4B shows typical spectral sensitivities for R, G and B wavebands as utilised for the approach described herein.

To simulate multi-spectral camera images of the scene, the incoming photons were first filtered into spectral bands and the incident angle was then used to further filter photons according to a geometrical camera model. In particular, an orthographic camera was simulated to avoid angular bias (in contrast, for a pin-hole camera, light at the edge of the image exits the tissue at a much shallower angle than that at the centre). RGB images were generated by filtering the multi-spectral (MS) data using filters corresponding to spectral sensitivity of a conventional RGB camera, see FIG. 4B. In particular, FIG. 4B shows a representative three channel RGB-like camera response curve. These response curves may be used, for example, to generate synthetic RGB data from the synthetic multispectral data (as described in more detail below). FIG. 4C then shows channel responses for the camera response curves of FIG. 4B for the oxygenated blood vessels (left) and the de-oxygenated blood vessels (right).

To validate data generated by the simulation, a separate simulation was performed using homogeneous tissue models. With these, multi-spectral image sets were generated in the same way as for those with the submerged vessels, and it was confirmed that the backscattered spectrum aligned with the expected result from theory. It was found that the homogeneous back scattered photon count was closely aligned to that predicted by theory when using the reduced scattering coefficient to calculate an effective attenuation.

Figure 5:
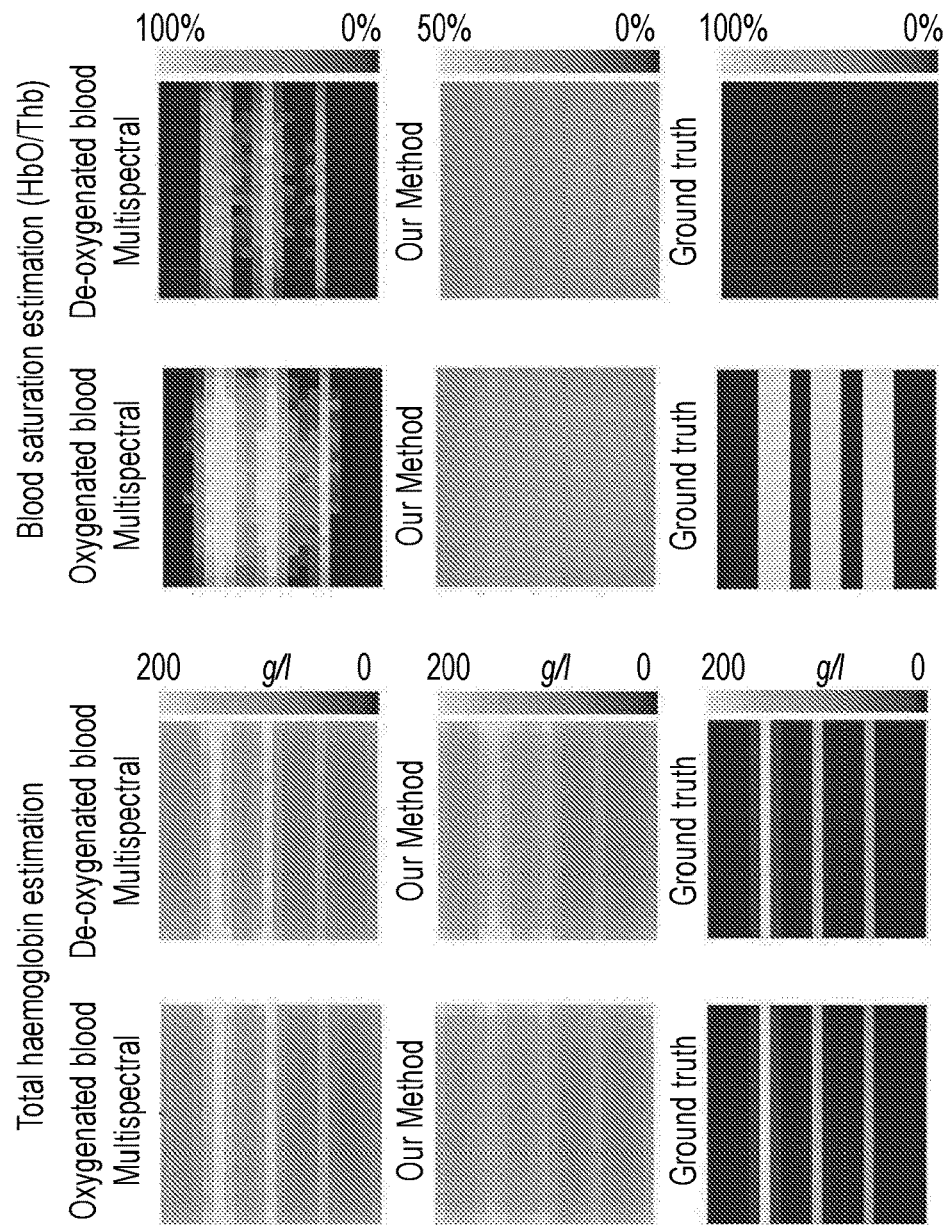
FIG. 5 shows a comparison of images depicting the estimation of total haemoglobin (left group) and oxygen saturation (right group) for oxygenated blood (left) and de-oxygenated blood (right) obtained firstly by using a multi-spectral linear fit (top row), secondly by using the method described (middle row), and thirdly from ground truth (lower row).
Figure 7:
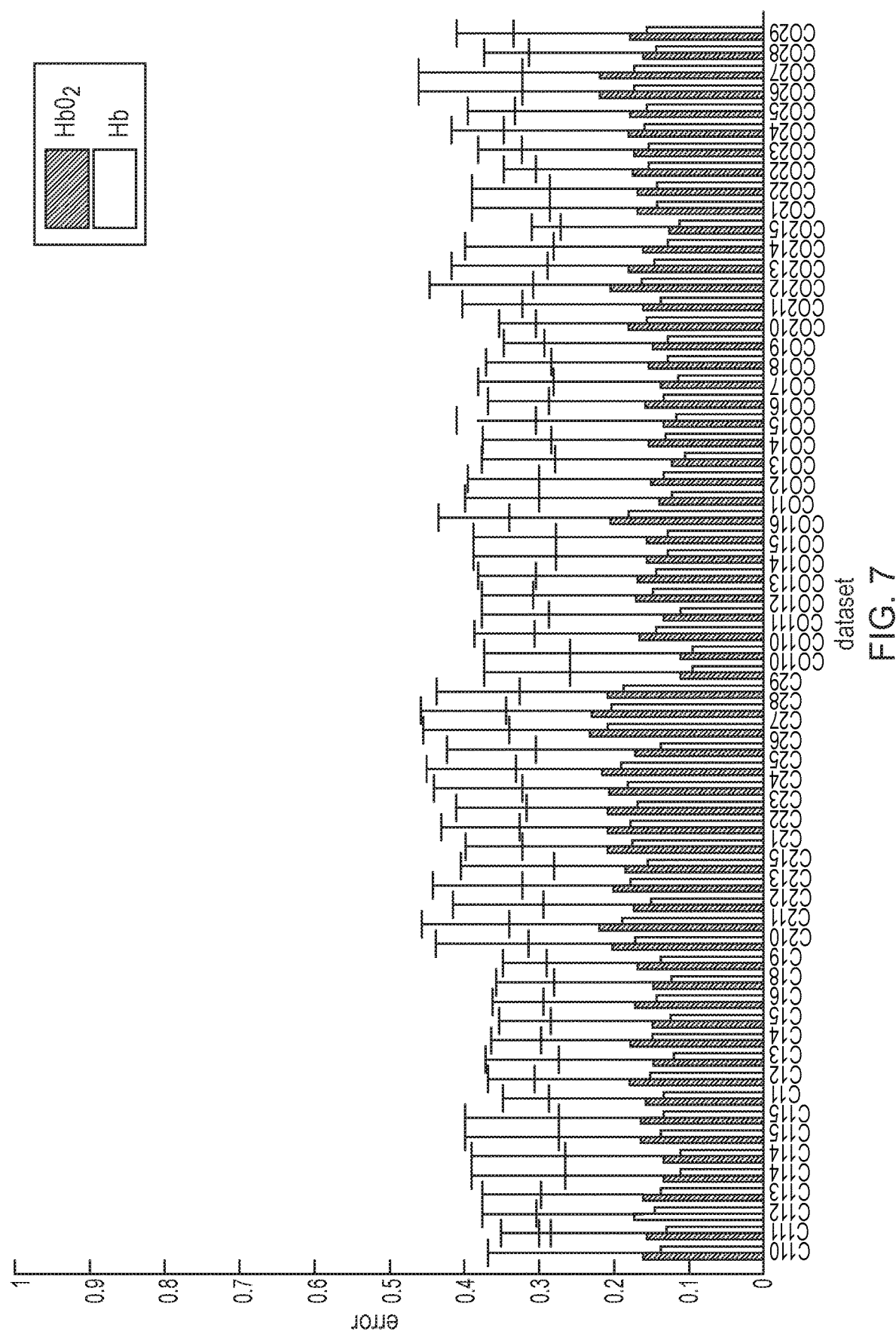
FIG. 7 is a graph showing the error between the estimated physical parameter of biological tissue (as obtained by the method described herein) and the ground truth for the in vivo experiment shown in FIG. 5.

The results of running the method of Example 1 on the synthetic data containing the three blood vessels to determine the concentration of both oxygenated and de-oxygenated haemoglobin is shown in FIG. 5. In particular, FIG. 7 shows a comparison of total haemoglobin and oxygen saturation estimation by multispectral linear fit (top row), and a method for estimating a physical parameter of biological tissue (second row) against the ground truth (third row), using the synthetic dataset. Results are show after histogram equalisation. The full multispectral approach localises well the total haemoglobin and saturation for both test cases. The method for estimating a physical parameter described herein is able to achieve reasonable localisation of total haemoglobin, while the saturation measure is less correlated to scene structures but does correctly differentiate between the two test cases. The apparent poor localisation for saturation is an artefact of the having very low values for both oxy and de-oxy haemoglobin in areas of soft tissue, since the saturation metric is very sensitive to slight noise for small values of oxy and de-oxy haemoglobin.

Overall, the best performance of FIG. 7 for both the multispectral and the approach described herein for Example 1 was in localising the total haemoglobin, and in this case, the method of Example 1 performs almost as well as the multispectral method. As noise levels, increase the variance of the multispectral approach increases at a faster rate than the method of Example 1. This is most likely due to the inherent smoothing that happens during the maximisation step from the application of the prior.

Both methods perform less well on the saturation estimation, and the method of Example 1 is generally less effective than the multispectral method, especially at high noise levels. This difference in the saturation estimation is likely due to the similarity of the attenuation spectra of oxygenated and de-oxygenated haemoglobin, which becomes even more subtle when marginalised by the camera into a three channel image. However, the method of Example 1 does distinguish in the correct manner, at a global whole image level, between the oxygenated tubes and de-oxygenated tubes (vessels) in the correct manner. Tabulated results are shown numerically in Table 1 below.

TABLE 1

The comparative performance between the multi-spectral technique and the RGB measurements described herein based on per-pixel absolute error with respect to the ground-truth, provided as mean and standard deviation)in g/l for the total haemoglobin error and as a proportion (0-1) for the saturation). The added zero mean Gaussian noise raw values were in the range [0, 1], hence the relatively small sigma values the for added noise. At each noise level, 100 uniquely seeded trials were run and the aggregate of all repetitions was then used to compute the error statistics.

| | Total haemoglobin error | | | |
| --- | --- | --- | --- | --- |
| | MS - THb | | RGB - THb | |
| noise ($\sigma$) | $\mu$ | $\sigma$ | $\mu$ | $\sigma$ |
| none | 30.9253 | 16.6138 | 34.1193 | 22.6741 |
| 0.01 | 31.3542 | 16.6520 | 35.8721 | 21.8864 |
| 0.03 | 32.8964 | 19.0817 | 38.8110 | 21.1776 |
| 0.05 | 37.1411 | 25.5051 | 41.7424 | 21.3663 |
| 0.07 | 41.6593 | 30.0078 | 45.1139 | 22.3773 |
| 0.09 | 44.5390 | 32.4252 | 49.0652 | 24.3692 |
| 0.10 | 45.3196 | 33.2666 | 50.9120 | 25.7727 |

| | Saturation error | | | |
| --- | --- | --- | --- | --- |
| | MS - Sat | | RGB - Sat | |
| noise ($\sigma$) | $\mu$ | $\sigma$ | $\mu$ | $\sigma$ |
| none | 0.2101 | 0.2641 | 0.2817 | 0.0813 |
| 0.01 | 0.2104 | 0.2643 | 0.2952 | 0.0775 |
| 0.03 | 0.2124 | 0.2679 | 0.3328 | 0.0745 |
| 0.05 | 0.2164 | 0.2781 | 0.3814 | 0.0842 |
| 0.07 | 0.2159 | 0.2863 | 0.4042 | 0.1016 |
| 0.09 | 0.2073 | 0.2881 | 0.4527 | 0.1250 |
| 0.10 | 0.2013 | 0.2874 | 0.4544 | 0.1332 |

It should be noted that the ground truth used in these this example influenced by two factors (at least): firstly the simulated imaging process is inherently noisy as it is the product of simulating the passage of a finite number of photons; and secondly there may be low level traces of haemoglobin in the tissue analysed by Bashkatov [10] (and as then used for determining the optical characteristics of the physical model for this example).

Real Data Experiments

Figure 6:
FIG. 6 shows an in vivo experimental set-up used as a test for the method described herein.

To further evaluate the method of Example 1, data was utilised from a porcine study, in which multispectral imaging was performed on tissue undergoing periods of artificially induced restricted blood flow. FIG. 6 is a schematic illustration of this approach. In particular, FIG. 6 shows an in vivo experimental set up used as a test subject for verifying the method described herein, in which the laparoscope can be seen entering the scene from the upper left side, while in the centre is a section of exposed bowel.

Using the method of Clancy [5], a ground truth total haemoglobin estimate was created for each multispectral set, masking out regions where the coefficient of determination (CoD) of this fit was lower then 0.5. To create corresponding input RGB data, the multispectral data was composited into a three channel image using known camera response curves for RGB (such as those shown in FIG. 4B).

In order to compare the results obtained using the method described herein against the multispectral generated ground truth, it is necessary to perform histogram equalisation (or some other suitable approach) to compensate for a scale ambiguity between the multispectral method and the approach described herein. This scale ambiguity is thought to arise from because the distance to the tissue surface is unknown and this has a significant effect by changing the global illumination. Nevertheless, it is possible to evaluate the relative distribution of estimated concentration by bring the results into the same scale, via histogram equalisation (for example).

FIG. 7 shows the mean absolute error between the estimates of a physical parameter (as described herein) and the ground truth computed from the multispectral data (lower errors therefore indicate a better correspondence to the ground truth). These errors are without units due to the histogram equalisation, but because the ground truth is normalised into the range [0,1], the error also lies within this range. Over all in-vivo data sets, the mean absolute error is 0.1394 with a standard deviation of 0.1715. These values lie towards the low end of the error range and hence are indicative of a similar estimation by both the method described herein and the multispectral generated the ground truth.

Figure 8:
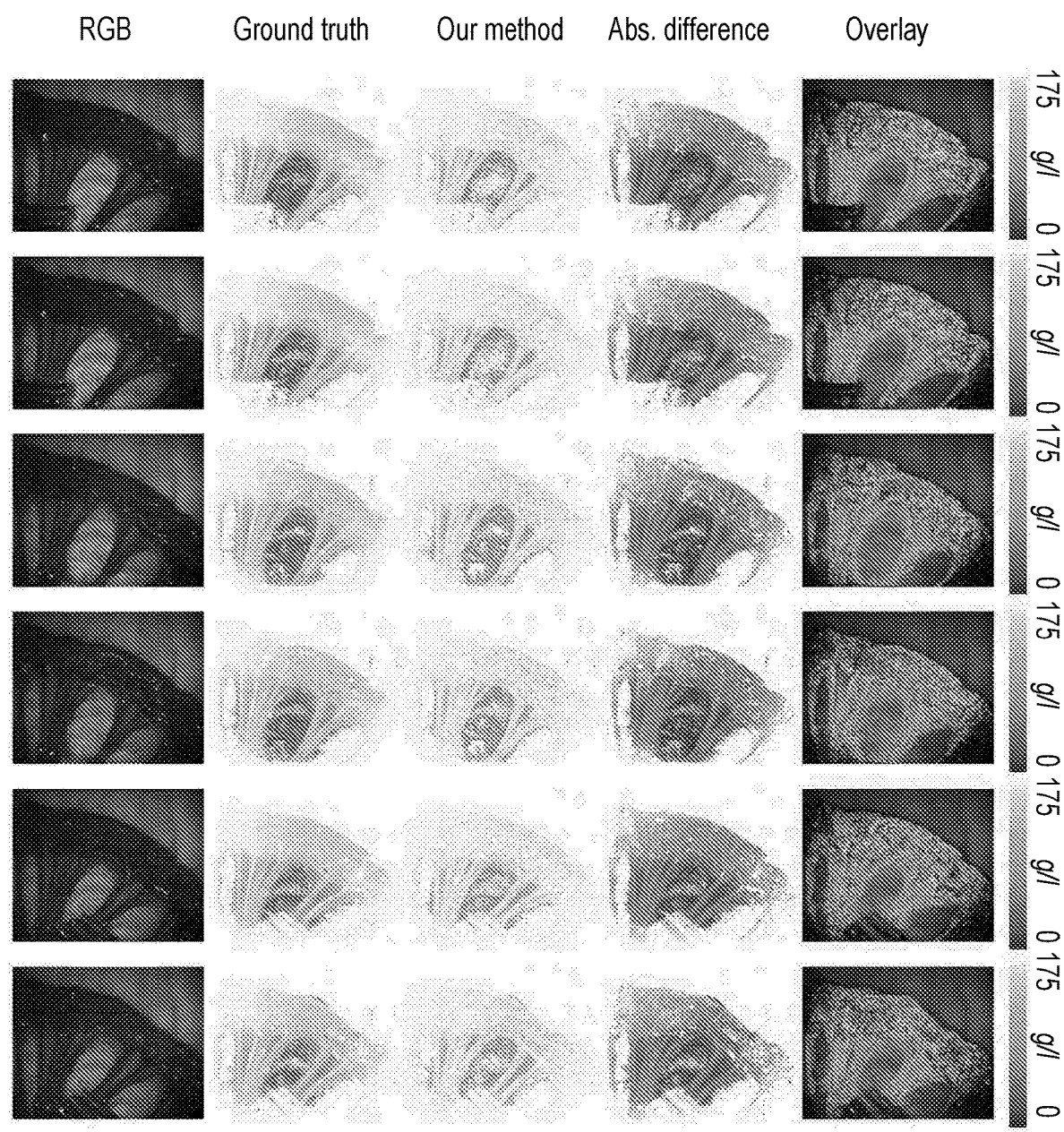
FIG. 8 shows examples (rows) each comprising an RGB image (left/first column) of in vivo biological tissue, the spatial distribution according to ground truth of total haemoglobin (second column), the spatial distribution using the method described herein of total haemoglobin (third column), the absolute difference between the second and third columns (fourth column), and an overlay (fifth column) of the absolute difference (fourth column) upon the corresponding RGB image (left column).

The similarity of the fitting can also be seen in FIG. 8, which shows a side-by-side comparison of the technique described herein, labelled "our method" in FIG. 8, alongside difference maps for the total haemoglobin measure. In particular, FIG. 8 shows a comparison for total blood volume (THb) maps, where the values are capped at 175 g/l for display purposes. All results and difference images in this Figure are displayed on the same scale. Clearly visible in the ground truth is the highly profuse region on the far left which corresponds to imaging artefacts where there is 0 in all the original multispectral data—a similar outlier region can be seen in the result for the method described herein near the top of the frame.

Example 2

Example 2 provides another example of using the method described herein as a real-time (or near real-time) technique for the measurement of physical (biological) parameters such as total haemoglobin and blood oxygenation in tissue. In Example 2, the method is performed using RGB images from a stereo laparoscope (although the method is equally applicable to other types of imaging equipment, including those that provide monocular images).

The high degree of spectral overlap between wavebands or channels such as RGB makes inference of haemoglobin concentration challenging, non-linear and under-constrained. In Example 2, the problem is decomposed into two constrained linear sub-problems with Tikhonov regularisation, and it is shown that this improves the estimation substantially, particularly in oxygenation accuracy, when using stereo image data rather than monocular images.

The approach described herein for Example 2 utilises a radiometric colour calibration of the laparoscopic imaging device, after which, the technique can be applied without modification of the laparoscopic instrumentation. The technique of Example 2 is validated both (i) on synthetic data using Monte Carlo simulation of light transport through soft tissue containing submerged blood vessels and (ii) on animal in vivo data with a hardware acquired multispectral data set for comparison.

Specifically, Example 2 provides a method for estimating blood oxygen saturation and total haemoglobin by using the RGB sensors (image capture device) in stereo laparoscopes. N.B. such RGB sensors are already the primary imaging device of stereo laparoscopes for providing robotic minimally invasive surgery.

The calibrated colour response curves of the RGB sensors define the mapping of (latent) multispectral data into RGB space. The approach of Example 2 inverts this process using a Tikhonov regularisation scheme to preserve smoothness. This reduces the problem into a two-step process, with the first of step having a closed form solution, enabling rapid processing of full frame stereo data.

Example 2 has been validated in a similar way to Example 1, namely, by using synthetic data generated from measured optical characteristics of blood [2] and sub mucosa [1] as input into the Mesh based Monte Carlo (MMC) simulation framework of Fang [12]. The technique of Example 2 is further validated on in vivo data by using the multispectral optimisation of Clancy [5] as the ground truth, and showing how the method of Example 2 correlates strongly with the results of such a full MSI analysis without the need for modified acquisition hardware. The results suggest how to acquire additional information during surgery by resolving the existing imaging RGB signal into the various wavebands.

Method

In general terms, the underlying approach of Example 2 matches that of Example 1. In particular, given a multispectral measurement comprising multiple non-overlapping waveband limited individual measurements $I_\lambda$, and corresponding vector of initial illumination $I_{0,\lambda}$, the estimation of the concentration parameter $\xi$ can be performed by least squares fitting (note that $\lambda$ typically corresponds to the wavelengths of the centre of each waveband). This result is obtained by first rearranging the Beer-Lambert equation for an individual wavelength:

$$-\log\left(\frac{I_\lambda}{I_{0,\lambda}}\right) = \xi a \quad (12)$$

The attenuation coefficients a for the chromophores of oxygenated ($HbO_2$) and de-oxygenated (Hb) haemoglobin are dependent on scattering and absorption characteristics. The attenuation coefficients are calculated a priori from a Monte Carlo simulation of the backscattered light and its attenuation in tissue. Such a simulation may be performed using similar techniques to those already described in relation to Example 1 above.

The requirement for the Beer-Lambert relation to hold is that the wavebands are non-overlapping and each is narrow. Given these conditions, this expression can be solved using a non negative least squares solver to ensure positivity. For example, the fast non-negative least squares (FNNSL) of Bro [15] is used in Example 2 to constrain the estimation of chromophore concentration from multispectral data.

In the case of RGB data, however, the measurement is actually in three channels, e.g., R, G, and B, each with significant spectral overlap and all fairly wide. In order to preserve the conditions of the Beer-Lambert equation, it would be necessary to pose the solution as the combination of three variably weighted sums of exponentials. Approaching this formulation directly becomes computationally intensive, but this can be mitigated by reducing the problem to two fast steps. First an estimate of the latent multispectral data (as received at the camera) is performed and then from this a least squares fitting can be performed in order to estimate the chromophore concentrations.

To estimate the multispectral image, $I_\lambda$, based on the captured RGB image data, $I_{RGBs}$, involves using the radiometric calibration of the camera C. One approach is to solve the linear system though a least squares minimisation such as:

$$I_\lambda = \arg\min_{I_\lambda} \|CI_\lambda - I_{RGBs}\|^2 \quad (13)$$

where $\|\cdot\|$ is the Euclidean norm.

Figure 9:
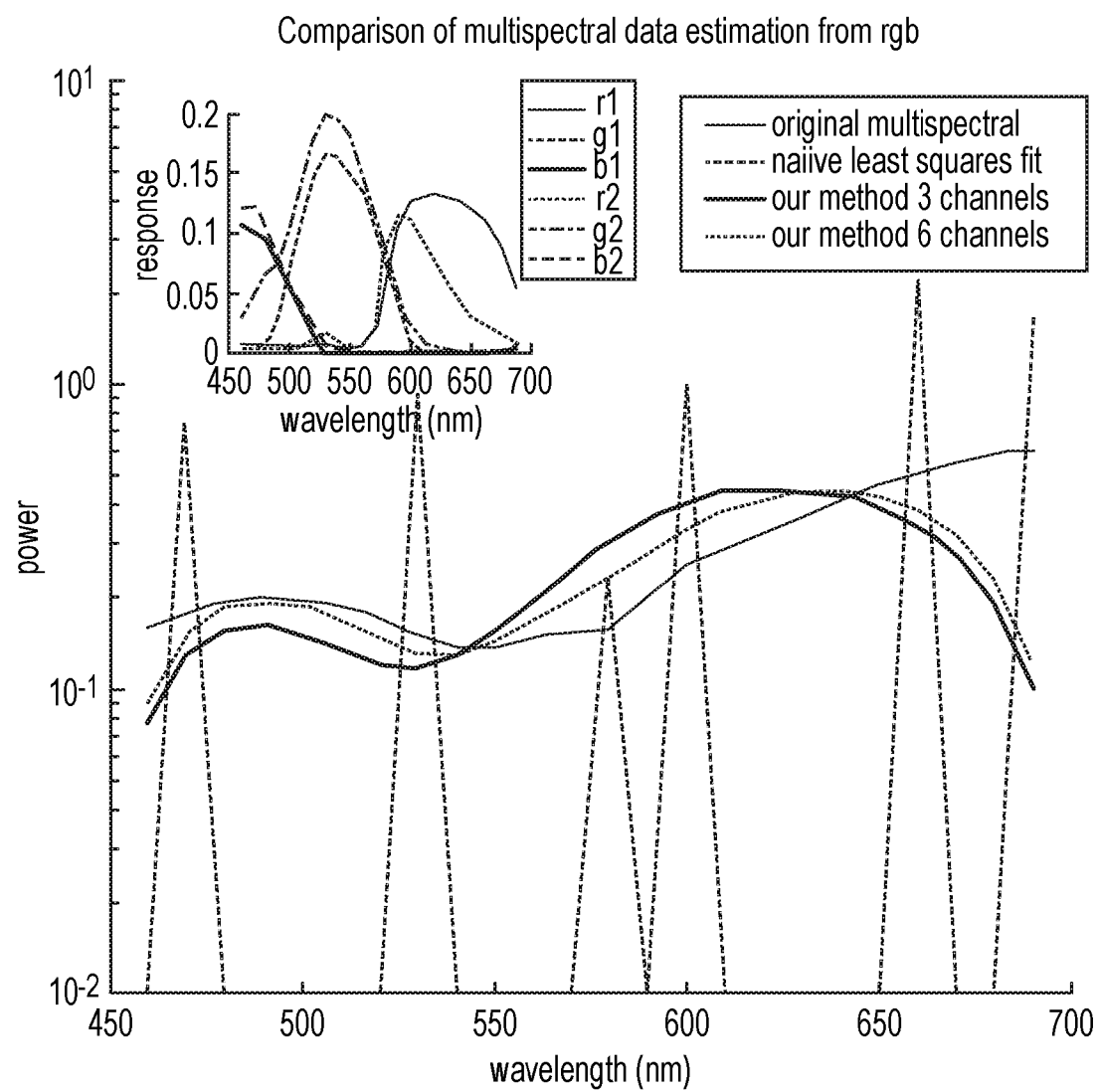
FIG. 9 is a plot showing original multispectral data (light blue) and the variation of power with wavelength, a least squares attempt to fit the original multispectral data (brown), a fit based on the approach described herein using 3 channels (RGB), and a fit based on the approach described herein using 2 sets of 3 channels (RGB) that are slightly different from one another.

However, this approach gives a poor estimation of the true multispectral data, since the problem is vastly unconstrained, given that $I_\lambda$ can have an order of magnitude more entries then $I_{RGBs}$, thus this solution is often a metamerism of the true multispectral data when viewed though this particular camera system. Typically such a least squares estimation tends to estimate multispectral data that has all of its variation in a small number of wavelength bands as shown in FIG. 9, which shows a comparative estimation of the multispectral data from RGB with a six channel sensor response inlet for reference.

To constrain the estimation, one can impose a prior ($\Gamma$) on $I_\lambda$, using a Tikhonov regularisation.

$$I_\lambda = \arg\min_{I_\lambda} \|CI_\lambda - I_{RGBs}\|^2 + \|\gamma\Gamma I_\lambda\|^2 \quad (14)$$

The prior, $\Gamma$, comprises the expected multispectral data that would be observed given the current estimate of the physical parameter of interest, $\xi$ for example, the haemoglobin concentration. The strength of the prior in Equation (14) is regulated by the scalar $\gamma=0.01$.

Equation (14) is typically solved implicitly as:

$$I_\lambda = (C^T C + \Gamma^T \Gamma)^{-1} C^T I_{RGBs} \quad (15)$$

where $\Gamma$ is often taken as the identity matrix, thus minimising the overall size of $I_\lambda$. However, for Example 2 we use a Laplacian matrix for $\Gamma$ to penalise a non-smooth $I_\lambda$, wherein the Laplacian matrix is formed of ones on the leading diagonal and negative half on the first super and sub diagonals. This choice of $\Gamma$ is made because the multispectral data is expected to be similar to that predicted by the Beer-Lambert relationship, which is mostly smooth across the visible wavelength range for a comprising attenuation due to oxygenated and de-oxygenated haemoglobin.

$$\mathrm{diag}(\Gamma) = \begin{bmatrix} 1 & -1/2 & 0 & 0 \\ -1/2 & \ddots & & 0 \\ 0 & & \ddots & -1/2 \\ 0 & 0 & -1/2 & 1 \end{bmatrix} \quad (16)$$

Once the multi-spectral data $I_\lambda$ has been estimated from the acquired RGB data, as above, using Equation 15, then a non-negative least squares solver can be used to estimate the concentration parameters. For example, the fast non-negative least squares (FNNSL) of Bro [15] may be used to perform the estimation of chromophore concentration from multispectral data $I_\lambda$ (as estimated from the acquired RGB data).

The method of Example 2 can also be applied to a monocular imaging context by reducing the number of columns in C and the length of $I_{RGBs}$. This allows for a concentration estimation to happen either jointly, utilising data from two or more sensors/cameras, or independently for each sensor/camera.

Experiments and Results

Synthetic Data Experiments

To create synthetic test data, multispectral image data was simulated and subsequently filtered to generate RGB camera responses broadly in line with the procedure described above with respect to Example 1. In particular, the optical characteristics of blood and colonic submucosa (soft tissue) were compiled from Bosschaart [9] and Bashkatov [10] respectively. The synthetic phantom model comprised a homogeneous block of soft tissue with three superficial vessels containing either oxygenated or de-oxygenated blood. The three blood vessels had different uniform diameters of 2 mm, 1 mm and 0.5 mm and the top edge of each vessel was at the same depth below the surface of the tissue at a depth of 1 mm.

The Mesh based Monte Carlo (MMC) simulation of Fang [12] was used on a meshed version of the digital phantom model as shown in FIG. 4A. The mesh was made denser near the blood vessel boundaries for smoother approximation of the curved vessel walls. For the MMC simulation, photons were generated at intervals of 10 nm across the range 400 nm to 900 nm. To detect the backscattered light, photon momentum was recorded for all photons leaving the bounds of the meshed region. Photons that did not exit through the side of the mesh that was illuminated were discarded, as were photons leaving at angles to the surface that were too oblique to be detected by a detector placed at 10 mm above the illuminated surface. Image data for each wavelength were then generated at this detector location. To simulate multi-spectral camera images of the scene the photons, the image data were filtered into by wavelength as appropriate.

RGB images were then generated by filtering the multispectral data using the spectral response curves for a conventional RGB camera—see for example the curve shown in FIG. 4B. Noise was added to the multispectral data by adding zero mean normally distributed vales to each wavelength channel. For the RGB images, noise was generated and correlated based on the spectral response curve of the camera (for each waveband), such that the mean noise level in each channel of the RGB images and multispectral data was equivalent.

Figure 10A:
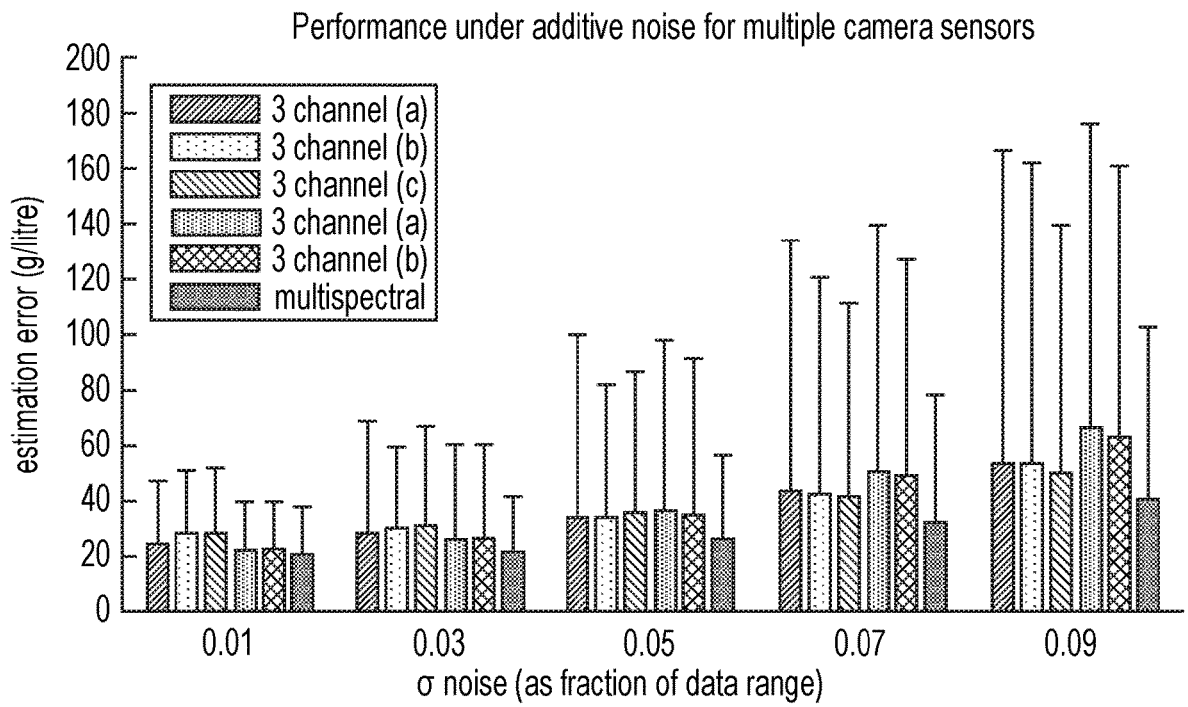
FIG. 10A shows the comparative absolute concentration estimation error for both oxygenated and deoxygenated haemoglobin combined across both test cases for Example 2 in the presence of noise.
Figure 10B:
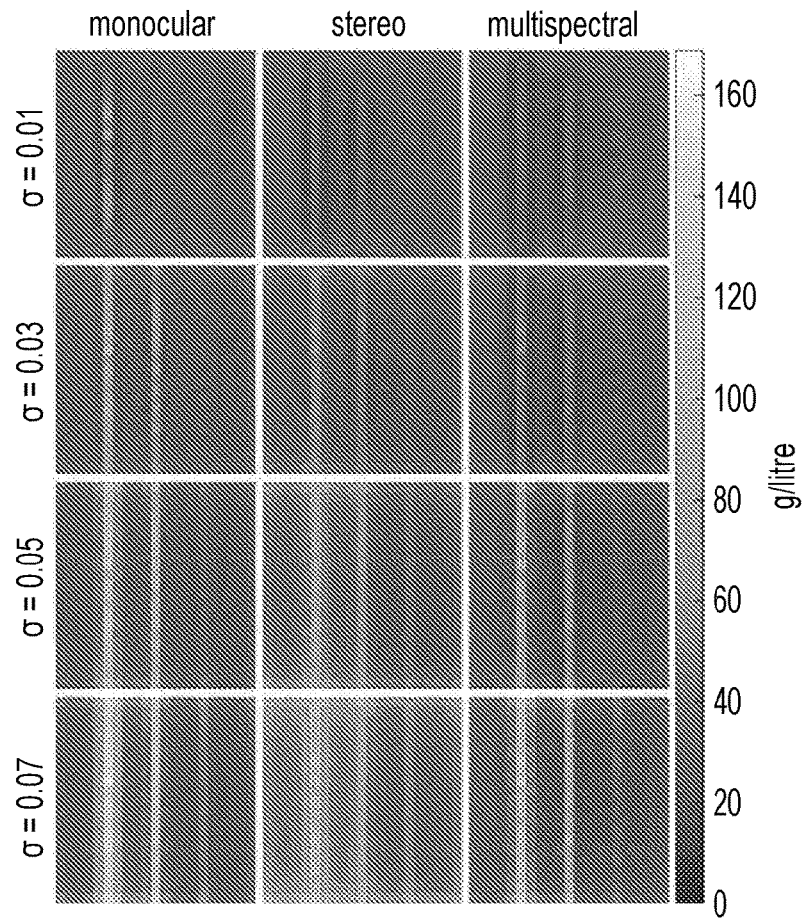
FIG. 10B shows the spatial distribution of the mean concentration estimation error for monocular (top), stereo (middle) and multispectral (bottom) at four noise levels.

The performance of the method of Example 2 is seen in FIGS. 10A and 10B. FIG. 10A shows the comparative absolute concentration estimation error for both oxygenated and deoxygenated haemoglobin combined across both test cases (for Example 2), showing mean absolute error (solid bar) and one standard deviation (thin line). For reference, typical total haemoglobin concentration for whole blood in an adult male is approx. 145 grams per litre. Noise is shown as a fraction of the sensor bit depth: for a typical 8 bit colour depth, a noise level of 0.09 corresponds to a sigma of 23.04 (i.e. 0.09*256). FIG. 10B represents the mean concentration estimation error for monocular, stereo and multispectral at four different noise levels at different image locations (the vertical lines correspond to the three blood vessels in each image).

As can be seen from FIGS. 10A and 10B, the approach described herein, based on performing an estimate from RGB images, is closer to the estimation from the full multispectral data as the noise level decreases. Also at low noise levels, the stereo (six channel) version of the method of Example 2 outperforms the monocular (three channel) version. However, at higher levels of noise the stereo version underperforms the monocular version due to the increased likelihood of over or under saturated pixel data in the six channels compared to the three of the monocular version. The impact of over or under saturated measurement data is more significant in the method of Example 2 compared to a multispectral approach because each channel in the method of Example 2 corresponds to a wide wavelength range. Consequently, in the presence of the smoothness prior on $I_\lambda$, this causes large global under or over chromophore concentration estimation. The presence of a few saturated outliers has less impact on the multispectral method as it is directly fitted against the multispectral data, and so the effect of a saturated outlier is localised to an individual wavelength band. (Note also that over and/or under saturation can be reduced or avoided by utilising an image capture device that has a greater colour bit depth for each pixel).

Real Data Experiments

To validate the accuracy of the method of Example 2 in an in vivo context, multispectral data sets, M, each comprising 24 non-overlapping 10 nm wide band limited images over the spectral range 460 nm to 690 nm were captured. Multispectral haemoglobin estimation using the method of Clancy [5] was performed on these data to establish a best case ground truth and the coefficient of determination (CoD) of this fit. A subset, M' of the original multispectral data where the CoD was over 0.5 was then utilised to create a multispectral data set in which there is high confidence in the ground truth concentration. From the multispectral data sets, corresponding RGB images were generated using typical RGB camera response curves such as shown in FIG. 4B.

We ran both the monocular and stereo versions of the method of Example 2 on M' and the regression from the RGB methods was compared against the ground truth. Concentrations of oxygenated and deoxygenated haemoglobin were then converted into the total haemoglobin and oxygen saturation measures, since these are the markers that would most normally be used to clinically evaluate a surgical site.

Figure 11A:
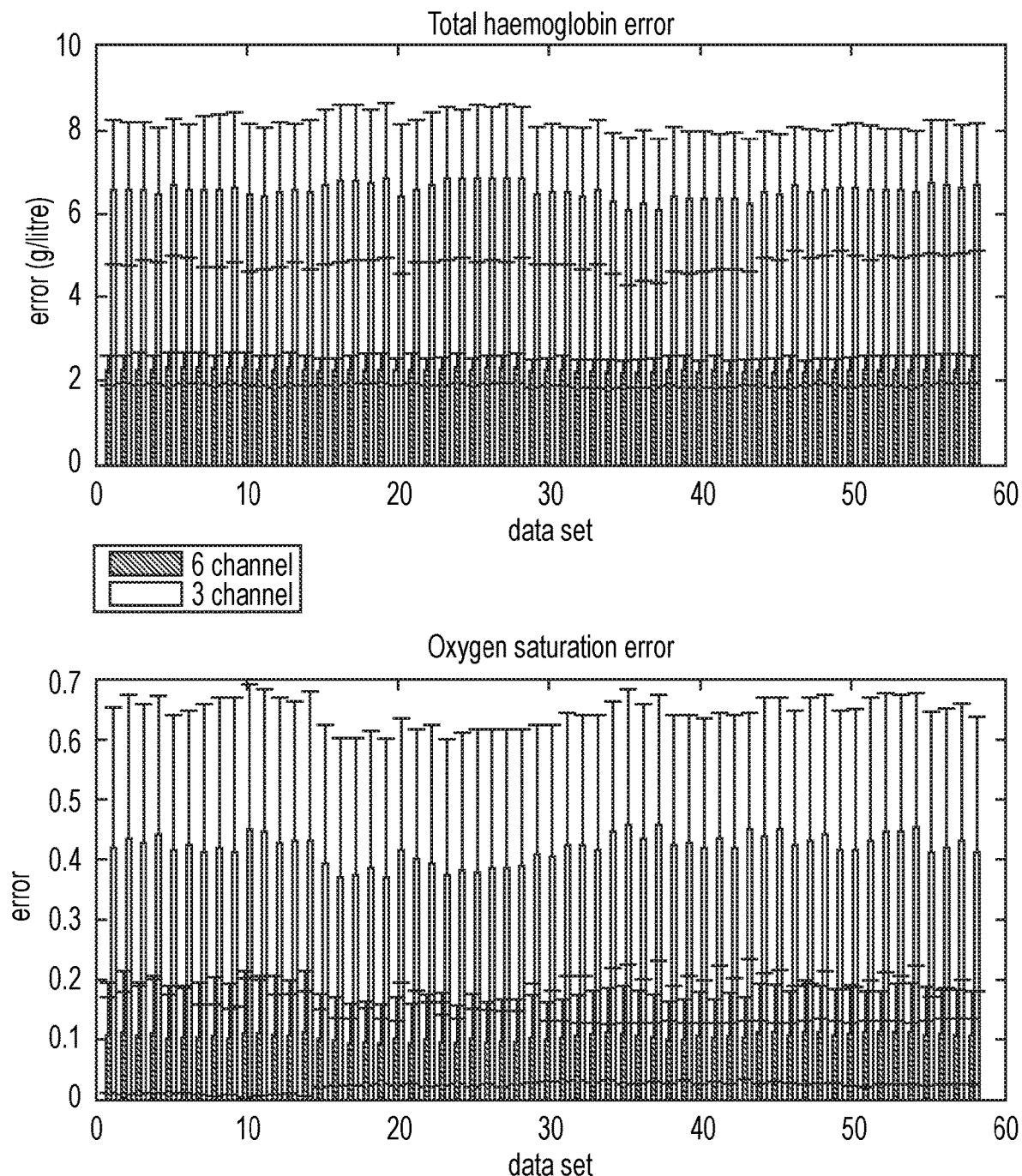
FIG. 11A is a graph comparing the performance of the three channel monocular against the six channel (stereo) version of the method of Example 2 with respect to total haemoglobin error (top) and total oxygen saturation error.

FIG. 11A shows the performance of the three channel monocular against the six channel versions of the method of Example 2 evaluated against the results from a full multispectral estimation with outliers removed via use of threshold. Clearly visible is the improved precision of the six channel method especially for the correct evaluation of the oxygen saturation. Overall, FIG. 11A shows that the use of stereo images significantly improves the estimation of total haemoglobin, with an overall mean absolute error of less than 3 g per litre when using six channels from two cameras, compared to over 6 g per litre for three channels with a monocular approach. The standard deviation of the error for these two methods remains close, but is slightly lower for the six channel variant. Given that total haemoglobin concentration of whole blood is in the region of 145 g/litre this indicates a high degree of accuracy when imaging for the purposes of perfusion mapping. Oxygen saturation estimation shows the most marked improvement when using stereo over monocular with an overall saturation estimation error of 10.27% down from 41.71% for the stereo and mono variants respectively. In evaluating the in vivo performance, results that corresponded to a THb concentration greater than 200 g/litre were considered outliers this enumerated as less than 0.1% of the results being rejected as outliers.

Figure 11B:
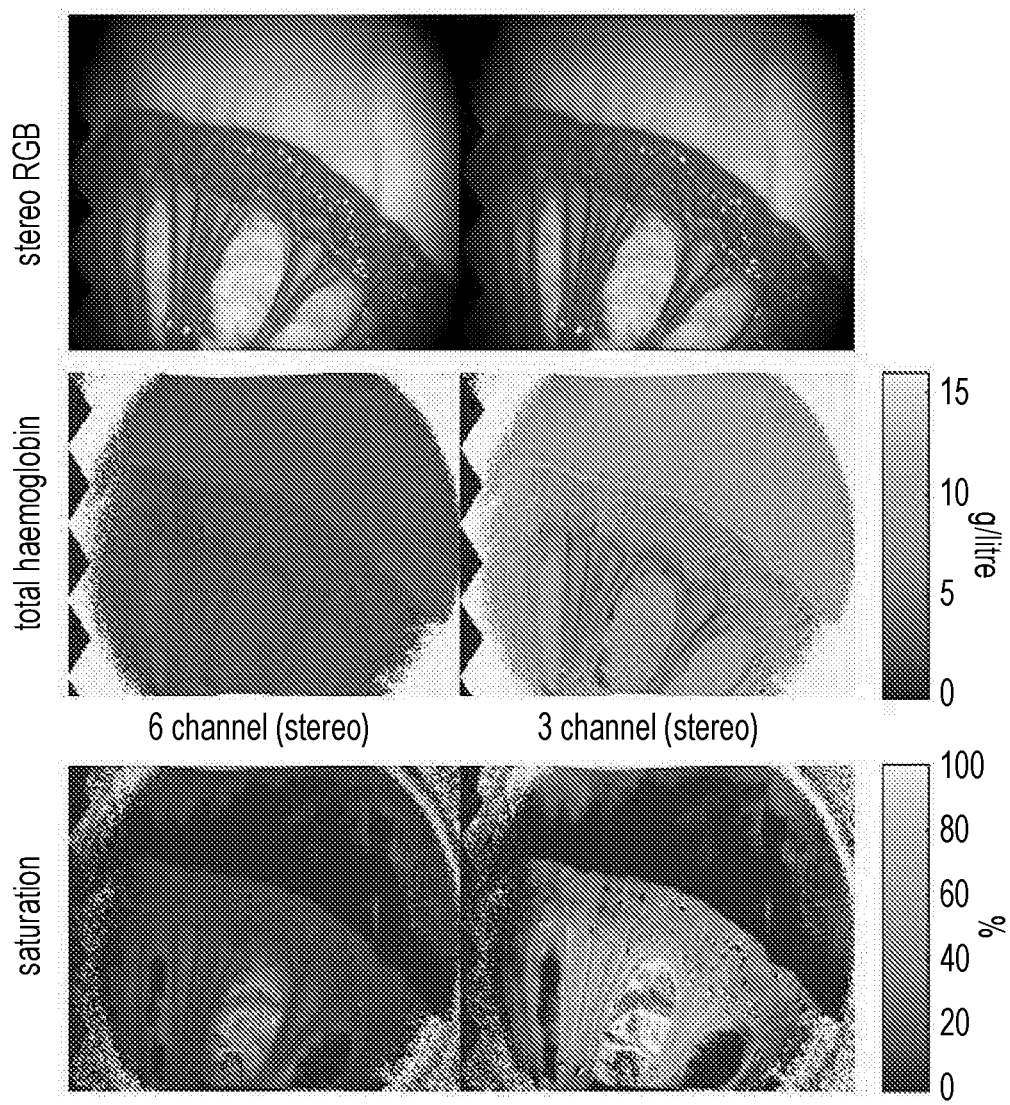
FIG. 11B shows (top) an RGB image of tissue from Example 2, (middle) the spatial distribution of total haemoglobin, and (bottom) the spatial distribution of oxygen saturation, showing 6-channel (stereo) to the left, and 3-channel (monocular) to the right.

In both cases, the method of Example 2 produces results which are similar to those from multispectral inference, and the error is typically located in areas not corresponding to vasculature. This is illustrated in FIG. 11B, where a section of bowel is exposed on a gauze background. FIG. 11B shows a stereo view of a surgical site with maps of the absolute difference in estimation of saturation and total haemoglobin between the method of Example 2 and that from full multispectral analysis. Note how the error is lower in places corresponding to locations of blood vessels. Furthermore, for the six channel case, the difference in total haemoglobin (from ground truth) is very low across the image, however the estimation of the saturation performs less well in images regions of low total haemoglobin. This is to be expected, as the oxygen saturation is a ratio of oxygenated to deoxygenated haemoglobin, and when both are at low concentration, small errors in the estimation of either become amplified in the aggregate saturation measure.

Further Implementations

Figure 12:
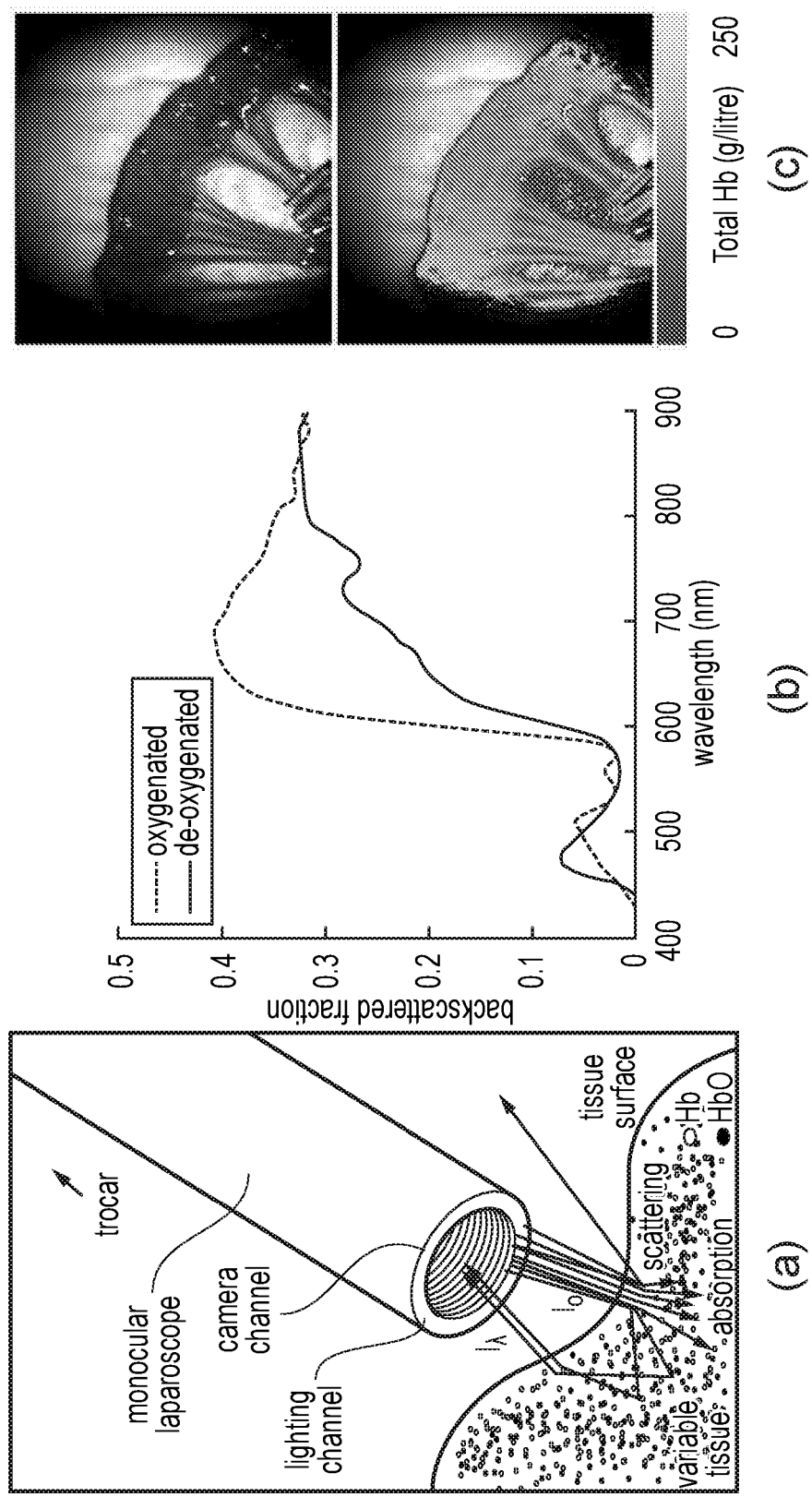
FIG. 12 is generally similar to FIG. 3, but shows another implementation using a monocular laparoscope, with a central camera channel, surrounded by an annular lighting arrangement.

FIG. 12 is generally similar to FIG. 3, but shows another implementation using a monocular laparoscope, with a central camera channel, surrounded by an annular lighting arrangement. In particular, FIG. 12a shows the passage of light through human tissue as a process comprising scattering and absorption events, with inhomogeneity in the concentration chromaphore resulting in a spatially varying distribution of detected light. The effective attenuation of a sample is due to a combination of the attenuation due to absorption as well as scattering. FIG. 12b shows the backscattered fraction of light for oxygenated and de-oxygenated blood under uniform illumination—this is generated from Monte Carlo simulation using [12]. This give us an aggregate attenuation coefficient ($-\log(\cdot)$ that combines attenuation due to absorption and scattering as well as the mean travel distance within tissue. FIG. 12C measures the total haemoglobin, formed by the sum of concentrations of these two chromaphores, with saturation then being determined as the ratio of oxygenated blood to total haemoglobin. Also, shown are an overlay (bottom) of the total haemoglobin, calculated from multispectral analysis, superimposed on the original endoscopic view (top).

Figure 13:
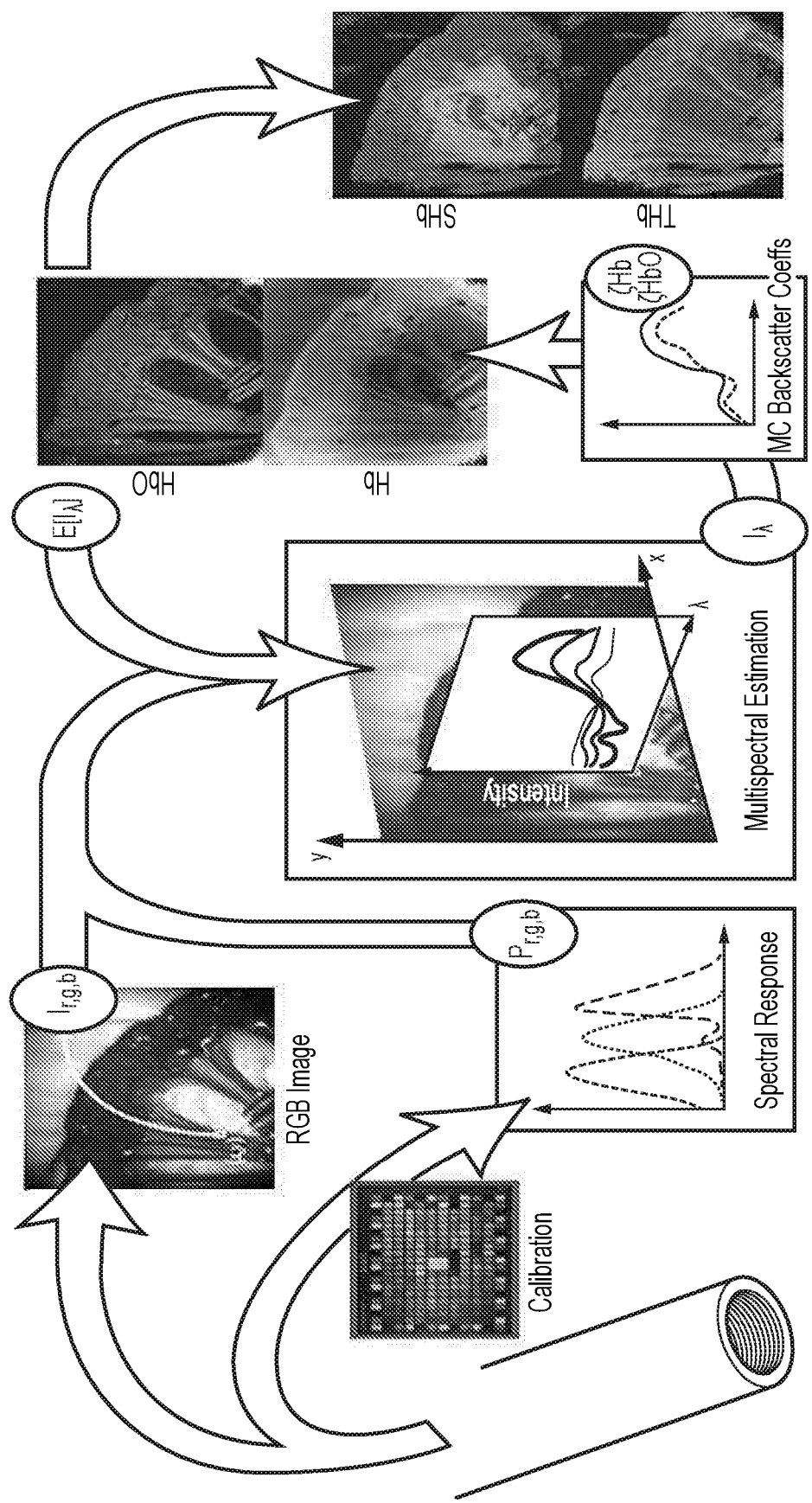
FIG. 13 presents an overview of the approach described herein for some implementations.

FIG. 13 presents an overview of the approach described herein for some implementations. The process includes capturing a spectral calibration for the laparoscope via a colour chart illuminated with the scopes standard lighting. When an RGB image is acquired from the laparoscope, for each pixel we alternately estimate the multispectral signal from the RGB data camera calibration and current concentrations estimate; then the concentrations estimate is updated from the current multispectral estimate and the Monte Carlo computed backscatter data.

It will be appreciated that in the approach of FIG. 13, the RGB image is generally already acquired for providing video guidance of the laparoscope. Accordingly, the concentration information derived from this RGB signal can be considered as extra results that are available without changing the existing clinical equipment or procedure (and hence with little or no additional cost or complexity). Note that this additional processing to obtain the concentration data from the RGB image may be performed in real-time (intraoperatively) and/or post-operatively, i.e. as a form of analysis of an RGB image obtained and recorded during an operative procedure.

In the implementations discussed above, the concentration estimation has generally been performed on a pixel by pixel basis. However, neighbourhood information might be used to improve this estimation (especially in conditions of higher noise level). In one simple approach, the pixels might be grouped together into larger blocks of pixel, and a separate estimation performed for each pixel block. Alternatively, the estimation may still be performed on a pixel-by-pixel basis, but information from neighbouring pixels may be used for the estimation procedure. Furthermore, in addition to spatial proximity, temporal proximity may also be used if the acquired image comprises a video sequence of images. For example, the estimated concentrations might be averaged over multiple frames to give a more accurate estimate. The skilled person will be aware of further methods for making use of such temporal and/or spatial proximity. (Note that the use of temporal proximity may require spatial alignment or registration of different images if/when the camera position moves; there are various known techniques for performing and/or enabling such alignment, e.g. by performing an image-to-image registration, or by fixing a tracking device to the laparoscope).

Further Discussion

As explained above, haemoglobin concentrations in tissue are important measurements that provide functional information and may also be used for the structural characterisation of tissue types. In minimally invasive surgery (MIS), the use of haemoglobin concentration imaging of tissue surfaces using multispectral imaging (MSI) is promising as a non-ionising optical imaging modality that can monitor organ viability in transplant procedures [20], [16] or be used to detect abnormal tissue. A major advantage of the MSI modality is that it is able to obtain wide field of view measurements without contact, thus allowing for monitoring large areas that cannot be observed through other sensing means, such as oxi-meter probes which can only give spot measurements.

Techniques for MSI compatible with MIS are typically limited for real-time monitoring by either their capture rate [5] or data processing speed [23], therefore limiting their use for imaging dynamic systems. Methods have been developed to estimate tissue haemoglobin concentrations for monitoring purposes using fast filter wheels of minimal sets of filters [6]. However, in MIS the surgical environment makes the use specialised hardware complex, because additional regulatory and sterilisation requirements must be taken into account. Computational methods requiring minimal hardware modification and using existing hardware are therefore highly attractive. Computational techniques that utilise the laparoscopic RGB video feed for tissue monitoring at speeds greater than 15 Hz may require inflexible calibration [7], or have difficulty dealing with scene motion [17], or involve a trade-off in estimation accuracy of saturation ($SO_2$) against total haemoglobin (THb) [24].

Wavelet decompositions have been widely used in image processing to transform data into domain spaces where certain operations can be applied more efficiently or components of the signal with little entropy can be omitted [21]. Such a wavelet approach is described below, along with a proposed framework for processing frames of laparoscopic video by Haar decomposition. This approach allows a hybrid technique that involves the use of two separate algorithms to process the various components of the compressed data representation. In particular, because the Haar wavelet normally produces large numbers of zeros in the transformed data set, certain information is concentrated in relatively few coefficients that can therefore be processed more effectively. As described below, the RGB image data can therefore be processed to arrive at a surrogate MSI signal though a dual optimisation approach, which is particularly effective for fairly smooth signals, such as laparoscopic video data.

Method

Underpinning the hybrid technique is again the estimation of a signal surrogate to MSI but obtained from at least two images (e.g. RGB video frames). As for the examples described above, this technique may utilise knowledge of transmitted attenuation characteristics of tissue [9] and back-scattered attenuation coefficients derived by Monte Carlo (MC) simulation [12], to provide a model of the combined attenuation due to absorption and scattering [23] in the biological tissue (N.B. since the camera and light source are usually on the same side of the biological tissue, e.g. during laparoscopic imaging). The fitting to surrogate MSI data can be performed to satisfy the Beer-Lambert relation [5], as discussed above.

In the hybrid method, once an RGB image is captured, the 2D discrete Haar transform can be used to decompose the image into four components, three directional approximate derivatives and a residual low pass coefficient component. This decomposition can then be exploited for efficient computation, since it supports the use of (computationally) expensive estimation on less of the data ($1=2^{1+n}$ where n is the level of decomposition).

The matrix H can be expressed for an image window $I=\{I_{x,y}, I_{x,y+1}, I_{x+1,y}, I_{x+1,y+1}\}$ as:

$$\text{Haar}(I)=I*H \qquad (17)$$

given that the 2d Haar matrix is formed as:

$$H = 0.5 \cdot \begin{bmatrix} 1 & 1 & 1 & 1 \\ 1 & 1 & -1 & -1 \\ 1 & -1 & -1 & 1 \\ 1 & -1 & 1 & -1 \end{bmatrix}$$

Note that the first component in the matrix is just an average value of the four pixel square, in effect a low pass filter; the second and fourth columns are sensitive to variations along the x and y axes respectively, while the third column is sensitive to variability in xy (diagonal).

As this is a just a linear transformation, if we group each pixel data in windows of four elements we can include it in the construction of RGB data $I_{RGB}$ from the multispectral signal $I_\lambda$:

$$C \cdot I_\lambda \cdot H = I_{RGB} \cdot H \qquad (19)$$

for known camera spectral sensitivity matrix C. (Equation 19 is analogous to Equation 4 above, noting that $I_c$ of Equation 4, the channel intensity e.g. for R/G or B channels, corresponds to $I_{RGB}$ in Equation 19; in addition, Equation 19 also omits the Poisson photon counting statistics, i.e. approximating the received light signal as continuous, as per classical optics; see also Equation 13 above).

The least squares solution for Equation 19 being:

$$I_\lambda = ((C^T C)^{-r} C^T \cdot I_{RGB} \cdot H) \cdot H \qquad (20)$$

since $H=H^*$. Similarly for the Tikhonov regularise solution as used by [24], see also Equation 14 above, we can apply this method to the Haar transformed data as:

$$I_\lambda \cdot H = ((C^T C + \Gamma)^{-1} C^T \cdot I_{RGB} \cdot H \qquad (21)$$

where $\Gamma$ is the identity matrix multiplied by a small constant $\gamma$. Here we have used the same windowed grouping:

$$I_{RGB} = \{I_{RGB, x, y}, I_{RGB, x, y+1}, I_{RGB, x+1, y}, I_{RGB, x+1, y+1}\} \qquad (22)$$

corresponding to the multispectral window:

$$I_\lambda = \{I_{\lambda, x, y}, I_{\lambda, x, y+1}, I_{\lambda, x+1, y}, I_{\lambda, x+1, y+1}\} \qquad (23)$$

While this demonstrates how Tikhonov based estimation, such as used in Example 2 above, can be used on any of the Haar coefficients, to get better accuracy one can use a hybrid method in which the regularisation of Equation 21 is performed only on the sparse directional components—i.e., the three directional components. For the low-pass coefficients (corresponding to the first column of the 2d Haar matrix, the Bayesian method of [23] is utilised (see also example 1 above), since this Bayesian method is more accurate than Tikhonov estimation. (Note that we can regard the low pass coefficients as analogous to an over-exposed image taken at a lower resolution).

Formally we can show that the method holds by substituting in the maximisation step of [23] with the low pass transformed data. Using $H_{LP}=0.54*[1, 1, 1, 1]$ to represent the low pass component of the discrete Haar transform, the concentration estimation $\hat{x}$ from low pass data is given by:

$$\xi \hat{x} = -\log(\lambda H_{LP}) \quad (24)$$

where $\xi$ are the backscatter attenuation coefficients for oxy and de-oxy haemoglobin ($HbO_2$ and $Hb$). We solve for $\hat{x}$ using least squares fitting, $$x=(-\xi'\xi)^{-1}\xi'\log(I_\lambda H_{LP}) \quad (25)$$

These concentration estimates are then used to generate the expected value for the multispectral data $E[I_\lambda]$ used to regularise then subsequent fitting iteration, this is defined as, $$E[I_\lambda]=e^{-\xi \hat{x}} \quad (26)$$

substituting the concentration estimate from (24) and cancelling terms the expected value will be the multispectral data transformed by $H_{LP}$ $$E[I_\lambda]=I_\lambda H_{LP} \quad (26)$$

Note that this applies to the low pass coefficients because they are all positive and so all terms remain real throughout.

The expectation step of [23] is linear and so compatible with working on Haar transformed data. One change that we make to the expectation step is to change the prior on the expected spectrum from a value prior to a shape prior. We do this by computing the second derivative of $E[I_\lambda]$ and use that to regularise the second derivative of the estimated $I_\lambda$, since this better regularises the estimation.

As described above, once the surrogate MSI signal, $I_\lambda$, is found, the estimation of the physical parameter of the biological tissue can be obtained by solving the Beer-Lambert equation, or any other suitable equation relating the intensity of measured light and the absorption and scattering coefficients of the tissue.

Experiments and Results

We conducted two experiments to validate the proposed algorithm. The first experiment used RGB views generated from in vivo animal experiment MSI data sets, which allow a comparison of the method described herein to a hardware implemented gold standard. Secondly we utilised the method described herein to process video from a patch of tissue at the base of the tongue, showing that because we are able resolve at a high frame rate, we can detect the pulse rate by tracking a patch of tissue over time.

Comparison with Hardware Multispectral Imaging Signals

Real in vivo MSI data was used to generate synthetic RGB images using known camera spectral sensitivity curves, calibrated from the spectral response of cameras on a Da Vinci surgical robot [25]. The MSI data comes from experiments in which MSI was used to monitor and evaluate organ viability, by measuring tissue perfusion and oxygen saturation, throughout uterine transplant procedures performed on sheep and rabbits [20]. The data was chosen, inter alia, because it most closely resembles the envisioned clinical use for the method described herein. To evaluate computation speed and accuracy, we compared against [24] and [23], however, to make a fair comparison of speed on the same architecture, we implemented both of these methods for GPU using the CUDA programming language from Nvidia. We performed two variants of the method described herein, corresponding to single (w1) and multilevel (w3: three levels) Haar decomposition. Here, the level of decomposition represents the number of times the Haar decomposition is applied, i.e., the number of times the differences between pixels are calculated. For all methods, the accuracy was compared against the results of estimation from directly using the MSI data [5].

FIG. 14A show selected bands (wavelengths) from a multispectral datacube, and a corresponding RGB view synthesised according to the hybrid method described herein (denoted X and y). FIGS. 14B and 14C show comparisons between the total haemoglobin (THb) estimate (g/litre) and oxygen saturation ($SO_2$)estimate (%) of tissue obtained from a reference multispectral image (left) and a corresponding estimate from synthesised RGB images (right).

As seen in FIGS. 14A to 14C, the estimation from the hybrid method bears a strong visual similarity to the result of direct estimation from MSI data, with two notable variations. Firstly, in the hybrid method there is much less noise in the estimation, which can be interpreted as due to each of the MSI images being moderately noisy due to their limit waveband (hence lower signal intensity). Such noise is inherently smoothed out when synthesising RGB data from the MSI datacube, as each RGB band integrates over many MSI bands due to the wider sensitivity of the respective colour channels. On the other hand, the RGB technique is less able to robustly estimate haemoglobin concentrations in areas of high illumination (this can be clearly seen in the $SO_2$ estimation near the top of FIG. 14C). In addition, the generally smoother appearance of the synthesised results means that local variations in the MSI signal are lost due to both the synthesis of the RGB image and subsequently due to the regularisation in our estimation approach. However, overall the hybrid method was closer to that of [23] than [24], as shown in Table 2 below.

TABLE 2

$HbO_2$ and Hb estimation accuracy on synthetic data compared to direct estimation from multispectral data [5].

| Method | Computational architecture | Execution time Hz | Mean squared error g/litre |
|---|---|---|---|
| Bayes [23] | CPU | 0.0671 | 25 |
| Tikhonov [24] | CPU | 0.282 | 54 |
| Bayes [23] | CUDA | 3.54 | 25 |
| Tikhonov [24] | CUDA | 43.5 | 54 |
| Proposed (w1) | CUDA | 12.7 | 36 |
| Proposed (w3) | CUDA | 14.4 | 36 |

In terms of computational performance, the timed results of haemoglobin estimation were made using mega-pixel sized input images. Timings were calculated including all pre-processing steps, which for the hybrid method described herein includes the initial Haar decomposition and final recomposition. Table 2 shows that the proposed hybrid method has a quicker estimation time than the Bayesian methods but a higher error, while conversely, the proposed hybrid methods are slower than the Tikhonov methods but have a much lower error. Table 2 also illustrates the diminishing returns for the for multileveled (w3) variant of the described method compared to the single decomposition level version (w1), in that these two variations both have the same error performance albeit with a small computational variation in terms of speed.

Experiments on In vivo Data From a Stereo-Laparoscope

We captured video of the base of the tongue of an adult male using a Da Vinci surgical robot's stereo laparoscope. The laparoscopic camera was calibrated to estimate the channel sensitivity. We tracked a patch of tissue using the method of [22] over time in both left and right cameras, and processed the two views separately. Tracking and image warping was necessary in order to remove residual motion artefacts due to tongue movement allowing visualisation of the spectral and temporal variation of a selected region within a spatio-temporally registered signal. We then compared the mean value of total haemoglobin as estimated from each view and observed a strong similarity in estimation over time. (There appears to be constant offset between the estimates from each view; this could be due to a slight miscalibration of the spectral response curve for one of the cameras).

We observed high frequency noise in the time series data, which might potentially be due to specular highlights moving as the tissue surface deformed and moved, or to imperfect tracking (which is to be expected given the relatively difficult conditions). Processing the registered video signal after warping using a low pass filter, we were able to observe a periodic signal in the derivative of the time series which was aligned in both views. We believe this to be representative of physiological signals within the tissue due to cardiovascular activity. By looking at the Fourier transform of the change in THb estimation, the power spectrum peaked between 0.76 and 0.84 seconds, which corresponds to periodic signal of between 71 and 79 cycles per minute— matching the heart rate of the subject during the experimental acquisition.

FIG. 15 illustrates the results discussed above. In particular, FIG. 15a shows the original RGB laparoscopic view for this data, FIG. 15b show the $SO_2$ estimation overlaid on the laparoscopic view, FIG. 15c shows the THb estimation overlaid on the laparoscopic view. FIG. 15d shows the tracked THb over time from the left and right camera feeds separately this is reasonably constant. FIG. 15e shows the derivative after smoothing the THb trace for each camera view (smoothing was performed due to large amounts of high frequency noise in the trace, believe to arise from roaming high-lights on tissue surface, and non-perfect tracking). FIG. 15f shows a frequency analysis of the change in THb over time; although there is a lot of noise, fitting a polynomial curve finds the peak at between 0.76 and 0.84 seconds.

Above has been described a hybrid method for estimating haemoglobin concentration from RGB images. The method improves on the computational speed, which is important for real-time clinical applications, and can potentially detect spatial and temporal variations in the oxy- and de-oxygenated blood flow within tissue close the exposed surface. The results on data from animal transplantation experiments illustrate the potential surrogate use of a hardware MSI approach as a translatable method for monitoring and evaluating organs intra-operatively.

As described above, a discrete Haar decomposition to separate individual video frames into low pass and directional coefficients, and a different multispectral estimation technique is used on each. An increase in speed may be achieved by using fast Tikhonov regularisation on the directional coefficients, and more accurate (but slower) Bayesian estimation on the low pass coefficients. Note that apart from the change in estimation procedure, the same processing steps as described above for Examples 1 and 2 may still be utilised. For example, a colour image (e.g. RGB) of a region of biological tissue is acquired from a single image capture device (e.g., an RGB camera), and the multispectral image, $I_\lambda$, is estimated, to allow determination of physical parameters of interest. As part of this estimation procedure, the image is filtered, for example by using a Haar decomposition, which derives image gradients. The Haar wavelet transformed images support the use of separate algorithms to process the various components of the transformed data because the directional coefficients tend to contain many small (or zero) values; hence information is concentrated in low pass coefficients, with the former making a relatively small contribution to the overall solution. Accordingly, a hybrid (dual optimisation) approach is adopted, in which the low pass coefficients are processed by a high accuracy estimation method (e.g. Bayesian or any other suitable method), while the directional coefficients are processed by a lower accuracy, but faster, method (e.g. Tikhonov regularisation, or any other suitable method). This increase in processing speed supports a higher frame rate, and so is particularly helpful for tracking temporal variation in signals (or for countering movement of the subject during imaging).

The skilled person will be aware of various modification to the approach described above. For example, the Bayesian estimation may be applied to one or more of the directional components of the Haar transformed data if so desired (e.g. to give a greater accuracy). Also, processing techniques described in relation to Example 1 and 2, e.g., such as use of an LUT to speed up calculation time, may also be employed in the hybrid method.

CONCLUSION

A method for estimating the value of a physical parameter of biological tissue, the method comprising: acquiring a colour image of the biological tissue; extracting from the colour image at least two images in respective optical wavebands having a different spectral sensitivity from one another; providing a physical model of the optical properties of the biological tissue, wherein the optical properties of the biological tissue are sensitive to the value of said physical parameter; and estimating the value of the physical parameter at a given location based on an intensity value at that location for each extracted image, wherein the estimating utilises the physical model of the optical properties of the biological tissue and the spectral sensitivity for each respective waveband.

The acquired colour image typically represents a single snapshot that obtains colour information simultaneously in each of said respective optical wavebands. For example, the acquired colour image typically comprises a red-green-blue (RGB) image, i.e. a single image that includes colour information for each of three colour wavebands. The processing can then extract red, green and blue images from the original RGB image.

Note that in many surgical procedures, such an RGB image is acquired anyway, e.g. for image-assisted surgery. Accordingly, the acquired image is already available for use in the estimation of the physical parameter, without requiring any additional imaging equipment or procedures. The approach described herein provides additional information to a clinician with little or no negative impact on a patient or the overall clinical procedure. For example, the output may comprise a map of the value of the physical parameter which can be superimposed in real-time onto the acquired colour image. To support such real-time operation, the values of the physical parameter, given different intensity values in different wavebands of the extracted images, may be pre-computed and stored in a look-up table.

In some cases the given location for which the physical parameter is determined corresponds to a single pixel of the image, while in other cases the given location corresponds to a region formed by multiple pixels of the acquired image. The region may potentially correspond to a given anatomical structure, which may be identified, for example, by a segmentation procedure.

In some cases, the physical parameter relates to blood flow in vasculature within the biological tissue. For example, a first physical parameter to be estimated may comprise the concentration of oxygenated haemoglobin and a second physical parameter to be estimated may comprise the concentration of de-oxygenated haemoglobin. Such oxygenation of the haemoglobin changes the colour of the blood (makes it redder) and hence is amenable to investigation by the approach described herein. Related physical parameters of interest include the total concentration of both oxygenated and de-oxygenated haemoglobin and the oxygen saturation within the haemoglobin. The skilled person will be aware of further physical parameters that impact the colour of tissue, and hence might be investigated in this manner.

In some implementations, the first and second colour images of the biological tissue are acquired using a stereoscopic image capture device. This may help to provide better estimates of the physical parameter, e.g. if the two cameras of the stereoscopic image capture device have slightly different RGB sensitivities, since this then provides additional data points for estimating the true spectrum arriving at the image capture point.

A variety of statistical and algorithmic approaches can be utilised to derive the physical parameter from the extracted images. For example, the estimation may be performed using a Bayesian approach by performing a maximisation of:

$$P(\alpha(L)|I_1(L) \ldots I_M(L)) = [P(I_1(L) \ldots I_M(L)|\alpha(L)) \times P(\alpha(L))]/[P(I_1(L) \ldots I_M(L)]$$

wherein $\alpha(L)$ represents the physical parameter to be estimated at location L, $I_1(L) \ldots I_M(L)$ are the respective intensity values of M extracted images (M≥2) at location L, and $P(\alpha(L))$ is an assumed prior distribution of $\alpha$, wherein $P(I_1(L) \ldots I_M(L)|\alpha(L))$ is determined using the physical model, and wherein the maximisation is performed with respect to $\alpha$. In some implementations, $P(I_1(L) \ldots I_M(L)|\alpha(L))$ is determined by firstly using the physical model to estimate $I_\lambda(L)$, which represents the spectral distribution of light from the biological tissue arriving at the image capture device, and secondly using the estimated $I_\lambda(L)$ and the spectral sensitivity for each respective waveband to determine $I_1(L) \ldots I_M(L)$, e.g. by minimising the sum of squared differences.

However, somewhat simpler approaches are also feasible, such as estimating the value of the physical parameter by the iterative steps of: predicting the intensity value at the given location for each optical waveband from the physical model using a current trial value of the physical parameter; determining the difference at the given location between the predicted intensity value and the intensity value from the extracted image for each optical waveband; if the determined difference is below a threshold, selecting the current trial value of the physical parameter as the estimated value, and if not, updating the current trial value and returning to perform said predicting step for a new iteration. The skilled person will be aware of further possible approaches for estimating the value of the physical parameter.

Another approach which can provide trade-offs between computational power required and errors in the estimation has been described, in which a Haar wavelet transformation is performed on the captured image data before being processed according to one or more of the Tikhonov and Bayesian techniques. Although the Haar wavelet transform has been described herein as a method of pre-processing the captured images, the skilled person will be aware of other suitable transforms (e.g., such as other types of wavelet transforms) that could be applied in a similar manner.

The apparatus described herein may perform a number of software-controlled operations. In such cases, the software may run at least in part on special-purpose hardware (e.g. GPUs) or on conventional systems with conventional processors. The software may be loaded into such hardware, for example, by a wireless or wired communications link, or may be loaded by some other mechanism—e.g. from a hard disk drive, or a flash memory device.

The skilled person will appreciate that various embodiments have been described herein by way of example, and that different features from different embodiments can be combined as appropriate. Accordingly, the scope of the presently claimed invention is to be defined by the appended claims and their equivalents.

REFERENCES

[1] S. P. Nighswander-Rempel, R. A. Shaw, J. R. Mansfield, M. Hewko, V. V. Kupriyanov, and H. H. Mantsch, "Regional variations in myocardial tissue oxygenation mapped by near-infrared spectroscopic imaging," *Journal of Molecular and Cellular* Cardiology, vol. 34, no. 9, pp. 1195-1203, 2002.

[2] E. Claridge, D. Hidović-Rowe, P. Taniere, and T. Ismail, "Quantifying mucosal blood volume fraction from multispectral images of the colon," in *Medical Imaging 2007: Physiology, Function, and Structure from Medical Images*, A. Manduca and X. P. Hu, Eds. SPIE-Intl Soc Optical Eng, mar 2007.

[3] N. T. Clancy, S. Saso, D. Stoyanov, V. Sauvage, D. J. Corless, M. Boyd, D. E. Noakes, M.-Y. Thum, S. Ghaem-Maghami, J. R. Smith, and D. S. Elson, "Multispectral imaging of organ viability during uterine transplantation surgery," in *Advanced Biomedical and Clinical Diagnostic Systems XII*. SPIE-Intl Soc Opt Eng, 2014.

[4] M. B. Bouchard, B. R. Chen, S. A. Burgess, and E. Hillman, "Ultra-fast multispectral optical imaging of cortical oxygenation, blood flow, and intracellular calcium dynamics," *Optics express*, vol. 17, no. 18, pp. 15 670-15 678, 2009.

[5] N. T. Clancy, D. Stoyanov, D. R. C. James, A. D. Marco, V. Sauvage, J. Clark, G. Z. Yang, and D. S. Elson, "Multispectral image alignment using a three channel endoscope in vivo during minimally invasive surgery," *Biomed. Opt. Express*, vol. 3, no. 10, pp. 2567-2578, October 2012.

[6] S. Wickert, N. T. Clancy, D. Stoyanov, S. Arya, G. B. Hanna, H.-P. Schlemmer, P. Sauer, D. Elson, and L. Maier-Hein, "Endoscopic sheffield index for unsupervised in vivo spectral band selection," 2014.

[7] I. Nishidate, T. Maeda, K. Niizeki, and Y. Aizu, "Estimation of melanin and hemoglobin using spectral reflectance images reconstructed from a digital RGB image by the wiener estimation method," *Sensors*, vol. 13, no. 6, pp. 7902-7915, jun 2013.

[8] Y. Fawzy, S. Lam, and H. Zeng, "Rapid multispectral endoscopic imaging system for near real-time mapping of the mucosa blood supply in the lung," *Biomedical Optics Express*, vol. 6, no. 8, p. 2980, 2015.
[9] N. Bosschaart, G. J. Edelman, M. C. G. Aalders, T. G. van Leeuwen, and D. J. Faber, "A literature review and novel theoretical approach on the optical properties of whole blood," *Lasers Med Sci*, vol. 29, no. 2, pp. 453-479, oct 2013.
[10] A. N. Bashkatov, E. A. Genina, V. I. Kochubey, V. S. Rubtsov, E. A. Kolesnikova, and V. V. Tuchin, "Optical properties of human colon tissues in the 350-2500 nm spectral range," *Quantum Electronics*, vol. 44, no. 8, pp. 779-784, aug 2014.
[11] L. Wang, S. L. Jacques, and L. Zheng, "Mcmlmonte carlo modeling of light transport in multi-layered tissues," *Computer methods and programs in biomedicine*, vol. 47, no. 2, pp. 131-146, 1995.
[12] Q. Fang, "Mesh-based monte carlo method using fast ray-tracing in plucker coordinates," *Biomed. Opt. Express*, vol. 1, no. 1, p. 165, 2010. Available: http://dx.doi.org/10.1364/BOE.1.000165
[13] J.-L. Boulnois, "Photophysical processes in recent medical laser developments: A review," *Lasers in Medical Science*, vol. 1, no. 1, pp. 47-66, 1986. [Online]. Available: http://dx.doi.org/10.1007/BF02030737
[14] D. T. Delpy, M. Cope, P. van der Zee, S. Arridge, S. Wray, and J. Wyatt, "Estimation of optical pathlength through tissue from direct time of flight measurement," *Physics in Medicine and Biology*, vol. 33, no. 12, pp. 1433-1442, dec 1988.
[15] R. Bro and S. D. Jong, "A fast non-negativity-constrained least squares algorithm," *J. Chemometrics*, vol. 11, no. 5, pp. 393-401, sep 1997.
[16] Clancy, N. T., Arya, S., Stoyanov, D., Singh, M., Hanna, G. B., Elson, D. S.: Intraoperative measurement of bowel oxygen saturation using a multispectral imaging laparoscope. Biomedical Optics Express 6(10), 4179 (sep 2015)
[17] Guazzi, A. R., Villarroel, M., Jorge, J., Daly, J., Frise, M. C., Robbins, P. A., Tarassenko, L.: Non-contact measurement of oxygen saturation with an RGB camera. Biomedical Optics Express 6(9), 3320 (2015)
"EMVA standard 1288: Standard for Characterization of Image Sensors and Cameras," European Machine Vision Association, no. 3.0, 2010. [Online]. Available: www.emva.org/wp-content/uploads/EMVA1288-3.0.pdf
[19] D. Pascale. (2012, Accessed: May 2016) Color checker data. [Online]. Available: http://www.babelcolor.com/colorchecker-2.htm#CCP2 data
[20] Clancy, N. T., Saso, S., Stoyanov, D., Sauvage, V., Corless, D. J., Boyd, M., Noakes, D. E., Thum, M. Y., Ghaem-Maghami, S., Smith, J. R., Elson, D. S.: Multispectral imaging of organ viability during uterine transplantation surgery in rabbits and sheep. Journal of Biomedical Optics 21(10), 106006 (2016), http://dx.doi.org/10.1117/1.JBO.21.10.106006
[21] Daubechies, I.: Ten Lectures on Wavelets. Society for Industrial & Applied Mathematics (SIAM) (January 1992), https://doi.org/10.1137%2F1.9781611970104
[22] Du, X., Clancy, N., Arya, S., Hanna, G. B., Kelly, J., Elson, D. S., Stoyanov, D.: Robust surface tracking combining features, intensity and illumination compensation. International Journal of Computer Assisted Radiology and Surgery 10(12), 1915-1926 (2015), http://dx.doi.org/10.1007/s11548-015-1243-9
[23] Jones, G., Clancy, N., Helo, Y., Arridge, S., Elson, D., Stoyanov, D.: Bayesian estimation of intrinsic tissue oxygenation and perfusion from RGB images. IEEE Transactions on Medical Imaging pp. 1-1 (2017), https://doi.org/10.1109%2Ftmi.2017.2665627
[24] Jones, G., Clancy, N. T., Helo, Y., Arridge, S., Elson, D. S., Stoyanov, D.: Inference of Tissue Haemoglobin Concentration from Stereo RGB, pp. 50-58. Springer International Publishing (2016), http://dx.doi.org/10.1007/978-3-319-43775-0_5
[25] Robu, M. R., Leclerc-Chalvet, M., Stoyanov, D.: Radiometric calibration for a spectrophotometric analysis pipeline for assessing burns. CRAS (sep 2015)

Acknowledgments

We thank Nvidia for the gracious donation of a Quado 6000 utilised in this work to generate results.

The invention claimed is:

1. A method for estimating the value of a physical parameter of biological tissue, the method comprising:
   Acquiring first and second colour images of the biological tissue using a stereoscopic image capture device;
   extracting, from each of the colour images, at least two images in respective optical wavebands having a different spectral sensitivity from one another, whereby a given location in the biological tissue is present in all of the extracted images from the first and second colour images;
   providing a physical model of the optical properties of the biological tissue, wherein the optical properties of the biological tissue are sensitive to the value of said physical parameter; and
   estimating the value of the physical parameter at said given location based on an intensity value at that location for each extracted image, wherein the estimating utilises the physical model of the optical properties of the biological tissue and the spectral sensitivity for each respective waveband.

2. The method of claim 1, wherein each of the acquired colour images represents a single snapshot that obtains colour information simultaneously in each of said respective optical wavebands.

3. The method of claim 2, wherein the at least two images extracted from each of the acquired colour images are spatially and temporally coincident with one another.

4. The method of claim 1, wherein the respective optical wavebands are at least partly overlapping.

5. The method of claim 1, wherein the physical parameter relates to blood flow in vasculature within the biological tissue; and optionally:
   wherein a first physical parameter to be estimated comprises the concentration of oxygenated haemoglobin, a second physical parameter to be estimated comprises concentration of de-oxygenated haemoglobin, or both;
   wherein the physical parameter comprises total concentration of both oxygenated and de-oxygenated haemoglobin; or
   wherein the physical parameter comprises oxygen saturation within the haemoglobin.

6. The method of claim 1 further comprising:
   combining the first and second colour images to produce an acquired monocular colour image; and
   extracting, from the acquired monocular colour image, at least two images in respective optical wavebands having a different spectral sensitivity from one another, whereby a given location in the biological tissue is present in each of the extracted images.

7. The method of claim 1, further comprising providing information on the illumination of the biological tissue for use as part of the estimating.

8. The method of claim 1, further comprising estimating the value of a physical parameter of biological tissue at multiple locations in each of the acquired images to form a map showing a spatial distribution of the value of the physical parameter.

9. The method of claim 8, further comprising:
showing the map of the value of the physical parameter in conjunction with each of the acquired colour images; or
showing the map of the value of the physical parameter superimposed onto each of the acquired colour images.

10. The method of claim 9, wherein the map is displayed in real-time during a clinical procedure on the biological tissue.

11. The method of claim 1, wherein the estimating includes using a Bayesian approach by performing a maximisation of:

$$P(\alpha(L)|I_1(L)\ldots I_M(L))=[P(I_1(L)\ldots I_M(L)|\alpha(L))\times P(\alpha(L))]/[P(I_1(L)\ldots I_M(L)]$$

wherein $\alpha(L)$ represents the physical parameter to be estimated at location L, $I_1(L)\ldots I_M(L)$ are the respective intensity values of M extracted images (M≥2) at location L, and $P(\alpha(L))$ is an assumed prior distribution of $\alpha$, wherein $P(I_1(L)\ldots I_M(L)|\alpha(L))$ is determined using the physical model, and wherein the maximisation is performed with respect to $\alpha$.

12. The method of claim 11, in which $P(I_1(L)\ldots I_M(L)|\alpha(L))$ is determined by firstly using the physical model to estimate $I_\lambda(L)$, which represents the spectral distribution of light from the biological tissue arriving at the image capture device, and secondly using the estimated $I_\lambda(L)$ and the spectral sensitivity for each respective waveband to determine $I_1(L)\ldots I_M(L)$.

13. The method of claim 12, wherein $I_1(L)\ldots I_M(L)$ are determined from the estimated $I_\lambda(L)$ and the spectral sensitivity for each respective waveband by minimising the sum of squared differences.

14. The method of claim 1, wherein estimating the value of the physical parameter includes iteratively:
predicting the intensity value at the given location for each optical waveband from the physical model using a current trial value of the physical parameter;
determining a difference at the given location between a predicted intensity value and the intensity value from the extracted image for each optical waveband;
if the determined difference is below a threshold, selecting a current trial value of the physical parameter as the estimated value, and if not, updating the current trial value and returning to perform said predicting for a new iteration.

15. The method of claim 1, wherein the method comprises filtering the at least two extracted images prior to estimating the value of the physical parameter, and wherein estimating the physical parameter involves estimating the physical parameter using the physical model and the filtered images.

16. The method of claim 15, wherein the filtering performs a decomposition into a first component and a second component, wherein the second component has less entropy, is relatively sparse compared to the first component, or both.

17. The method of claim 16, wherein estimating the value of the physical parameter involves applying a first estimation process to the first component and a second estimation process to the second component, wherein the first estimation process is slower but more accurate than the second estimation process.

18. A non-transitory computer readable medium comprising instructions that, when implemented on a computer, cause the computer to perform the method of claim 1.

19. Apparatus for estimating a value of a physical parameter of biological tissue, the apparatus being configured to:
Acquire first and second colour images of the biological tissue using a stereoscopic image capture device;
extract, from each of the colour images, at least two images in respective optical wavebands having a different spectral sensitivity from one another, whereby a given location in the biological tissue is present in all of the extracted images from the first and second colour images;
provide a physical model of the optical properties of the biological tissue, wherein the optical properties of the biological tissue are sensitive to the value of said physical parameter; and
estimate the value of the physical parameter at said given location based on an intensity value at that location for each extracted image, wherein the estimating utilises the physical model of the optical properties of the biological tissue and the spectral sensitivity for each respective waveband.

* * * * *